US012668796B2

(12) United States Patent
Matsuo et al.

(10) Patent No.: US 12,668,796 B2
(45) Date of Patent: Jun. 30, 2026

(54) NUCLEIC ACID DRUG SUPPRESSING PRODUCTION OF MYOSTATIN GENE MRNA

(71) Applicants: KNC LABORATORIES CO., LTD., Hyogo (JP); NATIONAL UNIVERSITY CORPORATION KOBE UNIVERSITY, Hyogo (JP)

(72) Inventors: Masafumi Matsuo, Hyogo (JP); Kazuhiro Maeta, Hyogo (JP)

(73) Assignees: KNC LABORATORIES CO., LTD., Hyogo (JP); NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 155 days.

(21) Appl. No.: 17/618,177

(22) PCT Filed: Jun. 18, 2020

(86) PCT No.: PCT/JP2020/023917
§ 371 (c)(1),
(2) Date: Dec. 10, 2021

(87) PCT Pub. No.: WO2020/262184
PCT Pub. Date: Dec. 30, 2020

(65) Prior Publication Data

US 2022/0220478 A1 Jul. 14, 2022

(30) Foreign Application Priority Data

Jun. 26, 2019 (JP) ................................ 2019-118446

(51) Int. Cl.

| | |
|---|---|
| ***C12N 15/113*** | (2010.01) |
| ***A23K 20/153*** | (2016.01) |
| ***A23L 33/13*** | (2016.01) |
| ***A61K 31/712*** | (2006.01) |
| ***A61K 31/7125*** | (2006.01) |
| ***A61P 19/02*** | (2006.01) |
| ***A61P 19/08*** | (2006.01) |
| ***A61P 21/02*** | (2006.01) |

(52) U.S. Cl.
CPC .......... *C12N 15/113* (2013.01); *A23K 20/153* (2016.05); *A23L 33/13* (2016.08); *A61K 31/712* (2013.01); *A61K 31/7125* (2013.01); *A61P 19/02* (2018.01); *A61P 19/08* (2018.01); *A61P 21/02* (2018.01)

(58) Field of Classification Search
CPC ............. C12N 15/113; C12N 2310/11; A61K 31/712; A61K 31/7125; A61K 48/00; A61P 19/02
See application file for complete search history.

(56) References Cited

U.S. PATENT DOCUMENTS

| | | | | |
|---|---|---|---|---|
| 2005/0124566 | A1* | 6/2005 | Robin ............ | C12Y 103/01022 536/23.1 |
| 2016/0256570 | A1 | 9/2016 | Tadin-Strapps et al. | |
| 2019/0060488 | A1 | 2/2019 | Tadin-Strapps et al. | |

FOREIGN PATENT DOCUMENTS

| | | | |
|---|---|---|---|
| CN | 106086031 | 11/2016 | |
| JP | 2003-517580 | 5/2003 | |
| JP | 2017-500373 | 1/2017 | |
| WO | 00/43781 | 7/2000 | |
| WO | 2008/005019 | 1/2008 | |
| WO | WO-2008005019 A1 * | 1/2008 | ............ C07H 21/02 |

OTHER PUBLICATIONS

Dhuri et. al. (J. Clin. Med.,9(6), 2004), (Year: 2004).*
Wei et al. (Molecular therapy, vol. 24, 11, p. 1889-1891 2016 (Year: 2016).*
Han et al. (Int. Journal of Biochemistry & Cell Biology, vol. 45, Issue. 10, 2013) (Year: 2013).*
International Search Report issued Sep. 1, 2020 in International (PCT) Application No. PCT/JP2020/023917.
Extended European Search Report issued Oct. 24, 2023 in corresponding European Patent Application No. 20833586.9.
Partial European Search Report issued Jun. 21, 2023 in European Patent Application No. 20833586.9.
International Preliminary Report on Patentability issued on Dec. 28, 2021, in corresponding International (PCT) Application No. PCT/JP2020/023917.
Canadian Office Action issued Nov. 28, 2025 in corresponding Canadian Patent Application No. 3,142,918.
Coralie Bellefroid et al., “Lipid gene nanocarriers for the treatment of skin diseases: Current state-of-the-art”, Eur. J. Pharm. Biopharm. (2019), vol. 137, pp. 95-111.

* cited by examiner

*Primary Examiner* — Tracy Vivlemore
(74) *Attorney, Agent, or Firm* — Wenderoth, Lind & Ponack, L.L.P.

(57) ABSTRACT

An antisense oligonucleotide of 15-30 bases or a salt or a solvate thereof, wherein the antisense oligonucleotide has a nucleotide sequence complementary to a target site in exon 1 of the myostatin gene and is capable of inhibiting the production of the mRNA of the myostatin gene. A pharmaceutical drug, a food, a feed, an agent for promoting myocyte proliferation and/or hypertrophy, an agent for increasing muscle mass and/or inhibiting muscle weakness, an agent for inhibiting production of the mRNA of the myostatin gene, and an inhibitor of the function of myostatin, each of which comprises the above antisense oligonucleotide or a salt or a solvate thereof.

23 Claims, 11 Drawing Sheets

Specification includes a Sequence Listing.

```
Dog       atgcagagactgcaaatctgtgtttatatttacctgtttgtgctgattgttgctggccca    60
Cattle    atgcaaaaactgcaaatctctgtttatatttacctatttatgctgattgttgctggccca    60
Human     atgcaaaaactgcaactctgtgtttatatttacctgtttatgctgattgttgctggtcca    60
Pig       atgcaaaaactgcaaatctatgtttatatttacctgtttatgctgattgttgctggtccc    60
          ***** * ******* *** *************** *** **************** **

Dog       gtcgatctaagtgagaacagtgagcaaaaagaaaatgtggaaaaggaggggctgtgtaat    120
Cattle    gtggatctgaatgagaacagcgagcagaaggaaaatgtggaaaaagaggggctgtgtaat    120
Human     gtggatctaaatgagaacagtgagcaaaaagaaaatgtggaaaaagaggggctgtgtaat    120
Pig       gtggatctgaatgagaacagcgagcaaaaggaaaatgtggaaaaagaggggctgtgtaat    120
          ** ***** * ********* ***** ** ************** **************

Dog       gcatgtatgtggaggcaaaacactaagtcttcaaggatagaagccataaaaattcaaatc    180
Cattle    gcatgtttgtggagggaaaacactacatcctcaagactagaagccataaaaatccaaatc    180
Human     gcatgtacttggagacaaaacactaaatcttcaagaatagaagccattaagatacaaatc    180
Pig       gcatgtatgtggagacaaaacactaaatcttcaagactagaagccataaaaattcaaatc    180
          ******   *****  *********   ** *****  ********** ** ** ******

Dog       ctcagcaaacttcgcctggaaacggctcccaacatcagcagagatgctgtcagacaactc    240
Cattle    ctcagtaaacttcgcctggaaacagctcctaacatcagcaaagatgctatcagacaactt    240
Human     ctcagtaaacttcgtctggaaacagctcctaacatcagcaaagatgttataagacaactt    240
Pig       ctcagtaaacttcgcctggaaacagctcctaacattagcaaagatgctataagacaactt    240
          ***** ******** ******** ***** ***** **** ***** * * ********

Dog       ttgccgcgggctcctccgctgcgggagctgatcgaccagtacgacgtccagagggatgac    300
Cattle    ttgcccaaggctcctccactcctggaactgattgatcagttcgatgtccagagagatgcc    300
Human     ttacccaaagctcctccactccgggaactgattgatcagtatgatgtccagagggatgac    300
Pig       ttgcccaaagctcctccactccgggaactgattgatcagtacgatgtccagagagatgac    300
          ** **    ******** ** * *** ***** ** ****  ** ******** **** *

Dog       agcagcgacggctccctggaggacgacgactaccacgccaccaccgagacggtcattgcc    360
Cattle    agcagtgacggctccttggaagacgatgactaccacgccaggacggaaacggtcattacc    360
Human     agcagcgatggctctttggaagatgacgattatcacgctacaacggaaacaatcattacc    360
Pig       agcagtgatggctccttggaagatgatgattatcacgctacgacggaaacgatcattacc    360
          ***** ** *****  **** ** ** ** ** ***** *  ** ** **  ***** **

Dog       atgcccgccgaga    373
Cattle    atgcccacggagt    373
Human     atgcctacagagt    373
Pig       atgcctacagagt    373
          *****  * ***
```

NUCLEIC ACID DRUG SUPPRESSING PRODUCTION OF MYOSTATIN GENE MRNA

TECHNICAL FIELD

The present invention relates to a nucleic acid drug which inhibits the production of the mRNA of the myostatin gene.

BACKGROUND ART

Myostatin is one of TGF-β cell proliferation factors and is a protein encoded by the myostatin gene. Myostatin has an effect of inhibiting myocyte growth/hypertrophy. Therefore, since inhibiting the function of myostatin promotes myocyte growth/hypertrophy, myostatin has been attracting attention as a target of muscular atrophy therapy. Actually, antibodies to myostatin or antisense oligonucleotides (AOs), etc. which allow the production of out-of-frame mRNA by regulating the splicing of the myostatin gene have been developed (Non-Patent Documents No. 1 and No. 2). However, no clinically useful method of inhibiting myostatin has yet been established.

PRIOR ART LITERATURE

Non-Patent Documents

Non-Patent Document No. 1: St Andre et al. Skeletal Muscle 2017, 7; 25 Non-Patent Document No. 2: Kang et al. Mol Ther 2011, 19; 159-64

DISCLOSURE OF THE INVENTION

Problem for Solution by the Invention

It is an object of the present invention to provide a novel method of inhibiting myostatin.

Means to Solve the Problem

The myostatin (MSTN) gene has a simple structure with three exons. The present inventors have aimed at developing an antisense oligonucleotide (AO) targeting exon 1 of the MSTN gene. The present inventors have hence synthesized various types of AOs using ENAs as monomers that are complementary to sequences of splicing factor binding sites, etc. within exon 1. Each of the synthesized AOs was introduced into rhabdomyosarcoma cells, and MSTN mRNA expressed in those cells was semiquantified by RT-PCR. Then, AOs which decrease mRNA expression were identified (FIG. 3). Further, the present inventors have revealed that the myostatin signaling activity in cells is decreased by introduction of such AOs (FIG. 8). These results showed that the identified AOs have an effect of inhibiting myostatin expression and eventually decreasing myostatin signaling. The present invention has been achieved based on these findings.

A summary of the present invention is described as below.

(1) An antisense oligonucleotide of 15-30 bases or a salt or a solvate thereof, wherein the antisense oligonucleotide has a nucleotide sequence complementary to a target site in exon 1 of the myostatin gene and is capable of inhibiting the production of the mRNA of the myostatin gene.

(2) The antisense oligonucleotide or a salt or a solvate thereof of (1) above, wherein the nucleotide sequence of exon 1 of the myostatin gene is the nucleotide sequence as shown in SEQ ID NO: 1, and the target site in exon 1 of the myostatin gene is located within the region of nucleotide Nos. 22-420 of the nucleotide sequence as shown in SEQ ID NO: 1.

(3) The antisense oligonucleotide or a salt or a solvate thereof of (1) or (2) above, wherein the nucleotide sequence of the antisense oligonucleotide comprises a sequence consisting of at least 15 consecutive nucleotides in any one of the sequences as shown in SEQ ID NOS: 2-25 (wherein “t” may be “u”, and “u” may be “t”).

(4) The antisense oligonucleotide or a salt or a solvate thereof of any one of (1) to (3) above, wherein the antisense oligonucleotide has 18 bases.

(5) The antisense oligonucleotide or a salt or a solvate thereof of (4) above, wherein the nucleotide sequence of the antisense oligonucleotide is any one of the sequences as shown in SEQ ID NOS: 2-25 (wherein “t” may be “u”, and “u” may be “t”).

(6) The antisense oligonucleotide or a salt or a solvate thereof of any one of (1) to (5) above, wherein at least one nucleotide is modified.

(7) The antisense oligonucleotide or a salt or a solvate thereof of (6) above, wherein the sugar constituting the modified nucleotide is D-ribofuranose and the hydroxy group at 2'-position of D-ribofuranose is modified.

(8) The antisense oligonucleotide or a salt or a solvate thereof of (7) above, wherein D-ribofuranose is 2'-O-alkylated and/or 2'-0,4'-C-alkylenated.

(9) A pharmaceutical drug comprising the antisense oligonucleotide of any one of (1) to (8) above or a pharmaceutically acceptable salt or solvate thereof.

(10) The pharmaceutical drug of (9) above for preventing and/or treating a pathological condition and/or a disease in which myostatin is involved.

(11) The pharmaceutical drug of (10) above, wherein the condition and/or disease in which myostatin is involved is muscular atrophy.

(12) The pharmaceutical drug of (11) above, wherein muscular atrophy is at least one selected from the group consisting of muscular dystrophy, myopathy, spinal muscular atrophy, sarcopenia and disuse muscle atrophy.

(13) The pharmaceutical drug of (10) above, wherein the condition and/or disease in which myostatin is involved is a condition and/or a disease in which a therapeutic effect is gained through muscle mass recovery.

(14) The pharmaceutical drug of (13) above, wherein the condition and/or disease in which a therapeutic effect is gained through muscle mass recovery is at least one selected from the group consisting of cancer cachexia, diabetes, cardiovascular diseases, renal diseases and bone diseases.

(15) The pharmaceutical drug of (14) above, wherein the cardiovascular disease is cardiac failure and/or arteriosclerosis; the renal disease is chronic renal failure; and the bone disease is inflammatory arthritis.

(16) A food comprising the antisense oligonucleotide of any one of (1) to (8) above or a salt or a solvate thereof that are acceptable as a food ingredient.

(17) A feed comprising the antisense oligonucleotide of any one of (1) to (8) above or a salt or solvate thereof that are acceptable as a feed ingredient.

(18) An agent for promoting myocyte proliferation and/or hypertrophy, comprising the antisense oligonucleotide or a salt or a solvate thereof of any one of (1) to (8) above.

(19) An agent for increasing muscle mass and/or suppressing muscle weakness, comprising the antisense oligonucleotide or a salt or a solvate thereof of any one of (1) to (8) above.

(20) An agent for inhibiting the production of the mRNA of the myostatin gene, comprising the antisense oligonucleotide or a salt or a solvate thereof of any one of (1) to (8) above.

(21) An inhibitor of the function of myostatin, comprising the antisense oligonucleotide or a salt or a solvate thereof of any one of (1) to (8) above.

(22) A method of preventing and/or treating a disease in which myostatin is involved, comprising administering to a subject an effective amount of the antisense oligonucleotide or a salt or a solvate thereof of any one of (1) to (8) above.

(23) A method of promoting myocyte proliferation and/or hypertrophy, comprising administering to a subject an effective amount of the antisense oligonucleotide or a salt or a solvate thereof of any one of (1) to (8) above.

(24) A method of increasing muscle mass and/or suppressing muscle weakness, comprising administering to a subject an effective amount of the antisense oligonucleotide or a salt or a solvate thereof of any one of (1) to (8) above.

(25) A method of inhibiting the production of the mRNA of the myostatin gene, comprising administering to a subject an effective amount of the antisense oligonucleotide or a salt or a solvate thereof of any one of (1) to (8) above.

(26) A method of inhibiting the function of myostatin, comprising administering to a subject an effective amount of the antisense oligonucleotide or a salt or a solvate thereof of any one of (1) to (8) above.

(27) The antisense oligonucleotide or a salt or a solvate thereof of any one of (1) to (8) above, for use in a method of preventing and/or treating a disease in which myostatin is involved.

(28) The antisense oligonucleotide or a salt or a solvate thereof of any one of (1) to (8) above, for use in a method of promoting myocyte proliferation and/or hypertrophy.

(29) The antisense oligonucleotide or a salt or a solvate thereof of any one of (1) to (8) above, for use in a method of increasing muscle mass and/or suppressing muscle weakness.

(30) The antisense oligonucleotide or a salt or a solvate thereof of any one of (1) to (8) above, for use in a method of inhibiting the production of the mRNA of the myostatin gene.

(31) The antisense oligonucleotide or a salt or a solvate thereof of any one of (1) to (8) above, for use in a method of inhibiting the function of myostatin.

Effect of the Invention

By means of the antisense oligonucleotide (AO) of the present invention, it is possible to inhibit the expression of myostatin and to thereby decrease myostatin signaling.

The present specification encompasses the contents disclosed in the specification and/or the drawings of Japanese Patent Application No. 2019-118446 based on which the present patent application claims priority.

MSTN pre-mRNA which is transcribed and produced from the MSTN gene comprises exon 1, exon 2 and exon 3. The present inventors prepared antisense oligonucleotides (AO1, AO2 and AO3) complementary to sequences within exon 1 of MSTN pre-mRNA.

Figure 2:
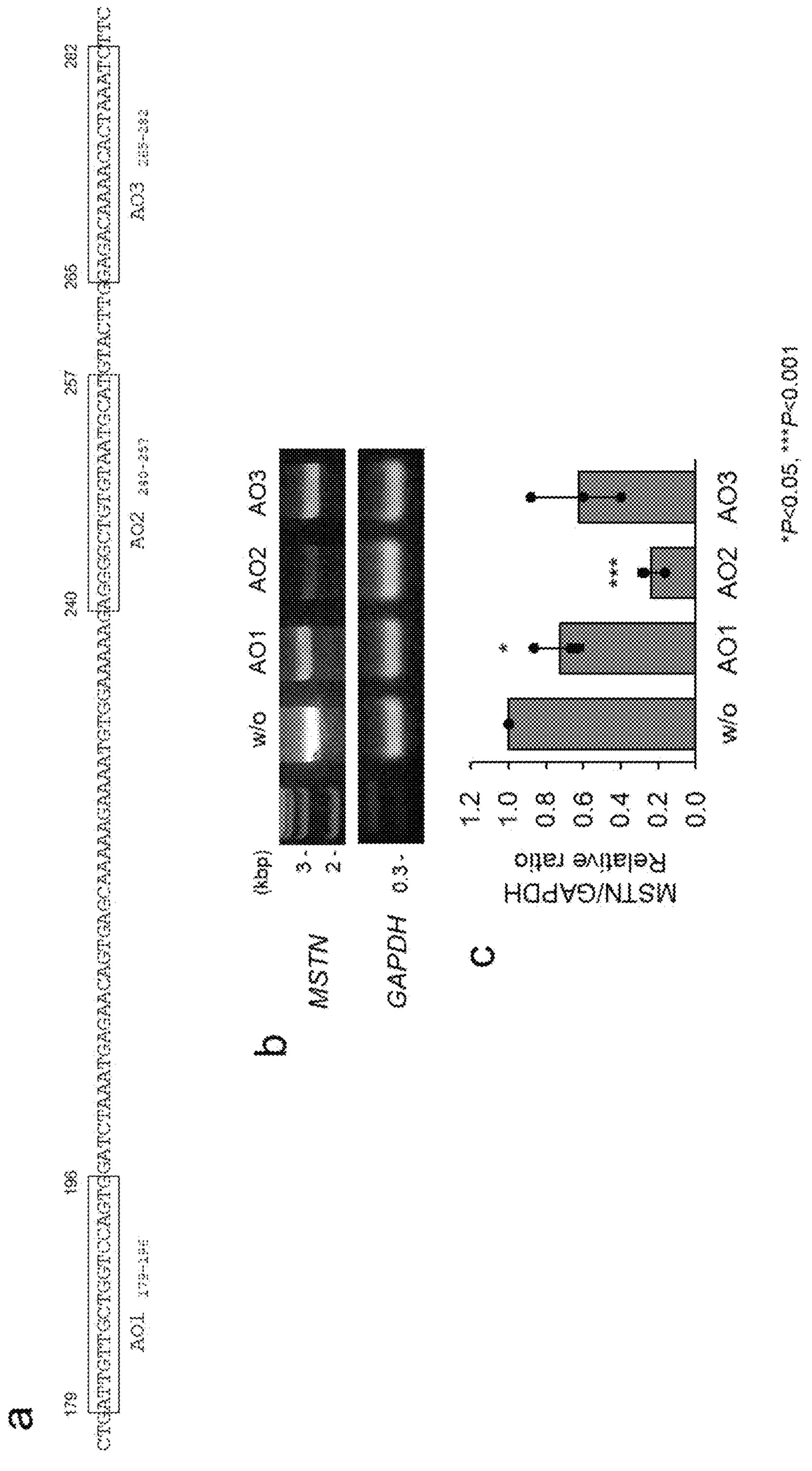

FIG. 2 Comparison of Efficacies of AO1, AO2 and AO3

Each AO was introduced into human rhabdomyosarcoma cells, and the resultant MSTN mRNA was analyzed by RT-PCR. The results are shown.

a) Complementary sequences to AO1, AO2 and AO3, respectively, are shown in boxes (Q). The numerical figures over the sequences (nucleotides 176-285 of SEQ ID NO:1) indicate the nucleotide numbers with the 5' end nucleotide of exon 1 of MSTN being taken as 1.

b) Results of RT-PCR on MSTN mRNA and GAPDH mRNA of human rhabdomyosarcoma cells are shown. “w/o” means without AO treatment.

c) Relative values are shown with the ratio of MSTN/GAPDH without AO treatment being taken as 1. *P<0.05, ***P<0.001.

Figure 3:
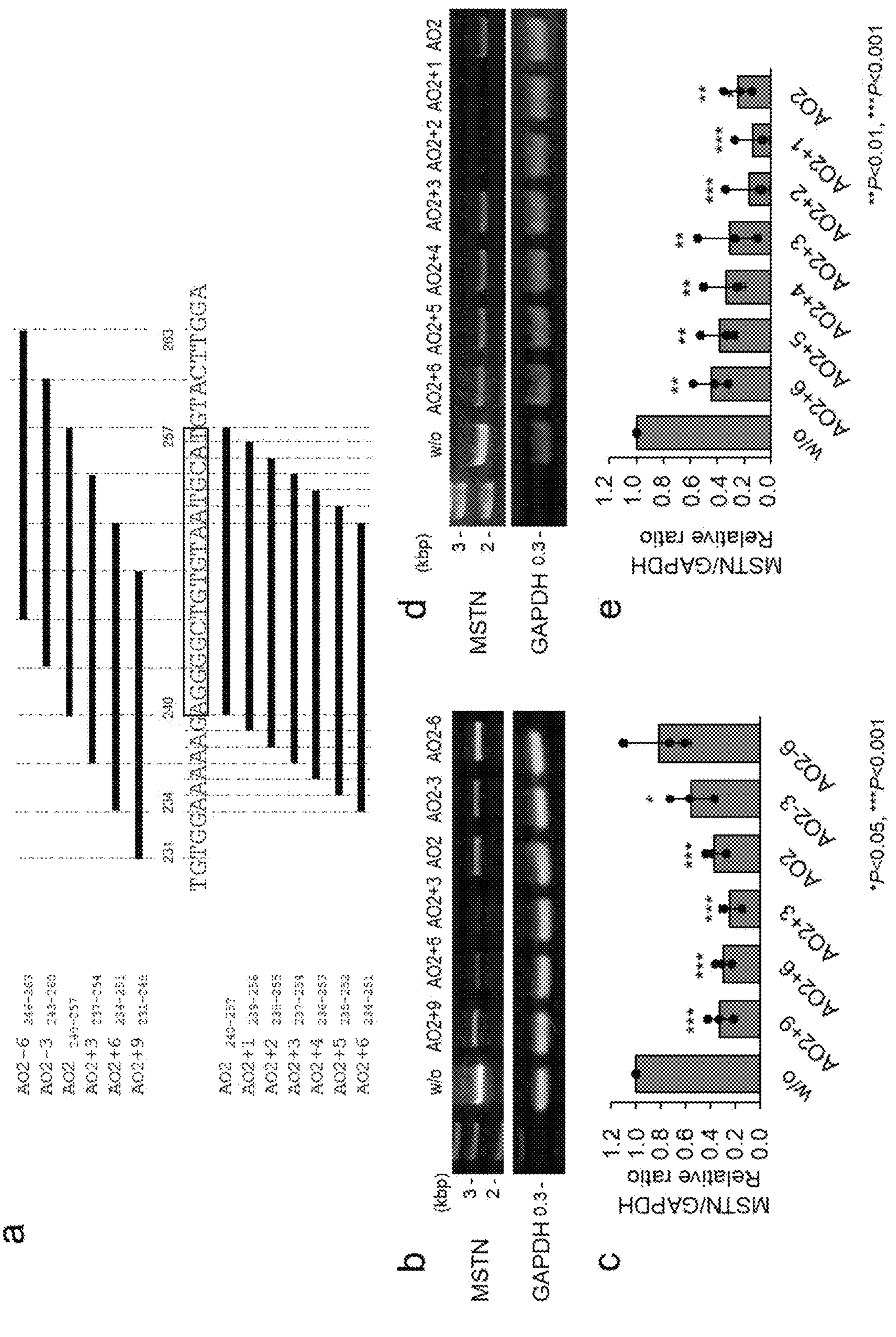

FIG. 3 Comparison of Efficacies of AOs Designed around AO2

Each AO was introduced into human rhabdomyosarcoma cells, and the resultant MSTN mRNA was analyzed by RT-PCR. The results are shown.

a) AOs are indicated by brackets and the complementary sequence to AO2 is shown in the box. Shown above this nucleotide sequence (nucleotides 229-266 of SEQ ID NO:1) are AOs which are shifted by increments of three bases toward either the 5' or 3' end as relative to the AO2 sequence. Shown below the nucleotide sequence (nucleotides 229-266 of SEQ ID NO:1) are AOs which are shifted by increments of one base toward the 3' end as relative to the AO2 sequence. The numerical figures over the nucleotide sequence indicate the nucleotide numbers with the 5' end nucleotide of exon 1 of MSTN being taken as 1.

b, d) Results of RT-PCR on MSTN mRNA and GAPDH mRNA of human rhabdomyosarcoma cells are shown. “w/o” means without AO treatment.

c, e) Relative values are shown with the ratio of MSTN/GAPDH without AO treatment being taken as 1. *P<0.05, P<0.01, *P<0.001.

Figure 4:
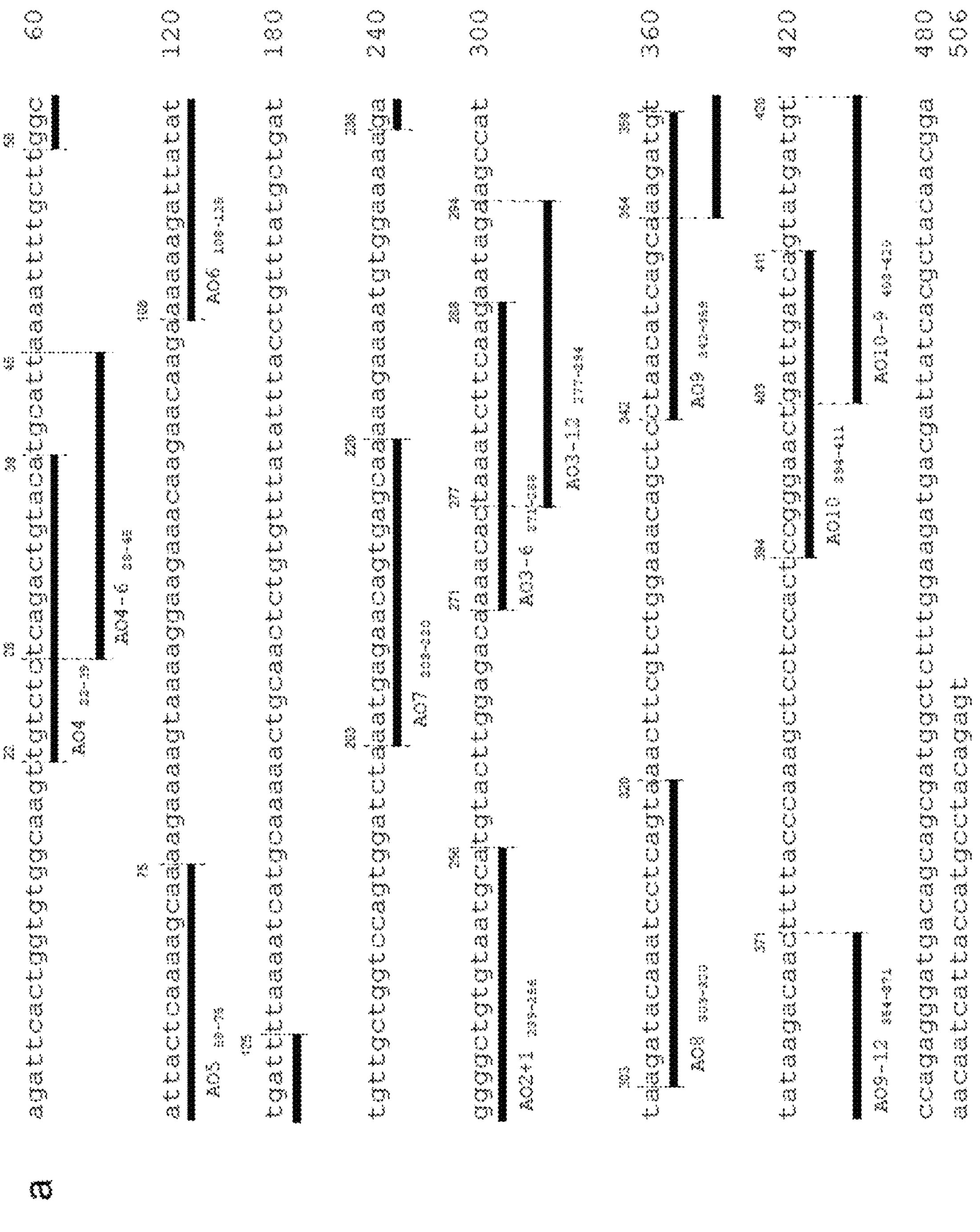
Figure 4:
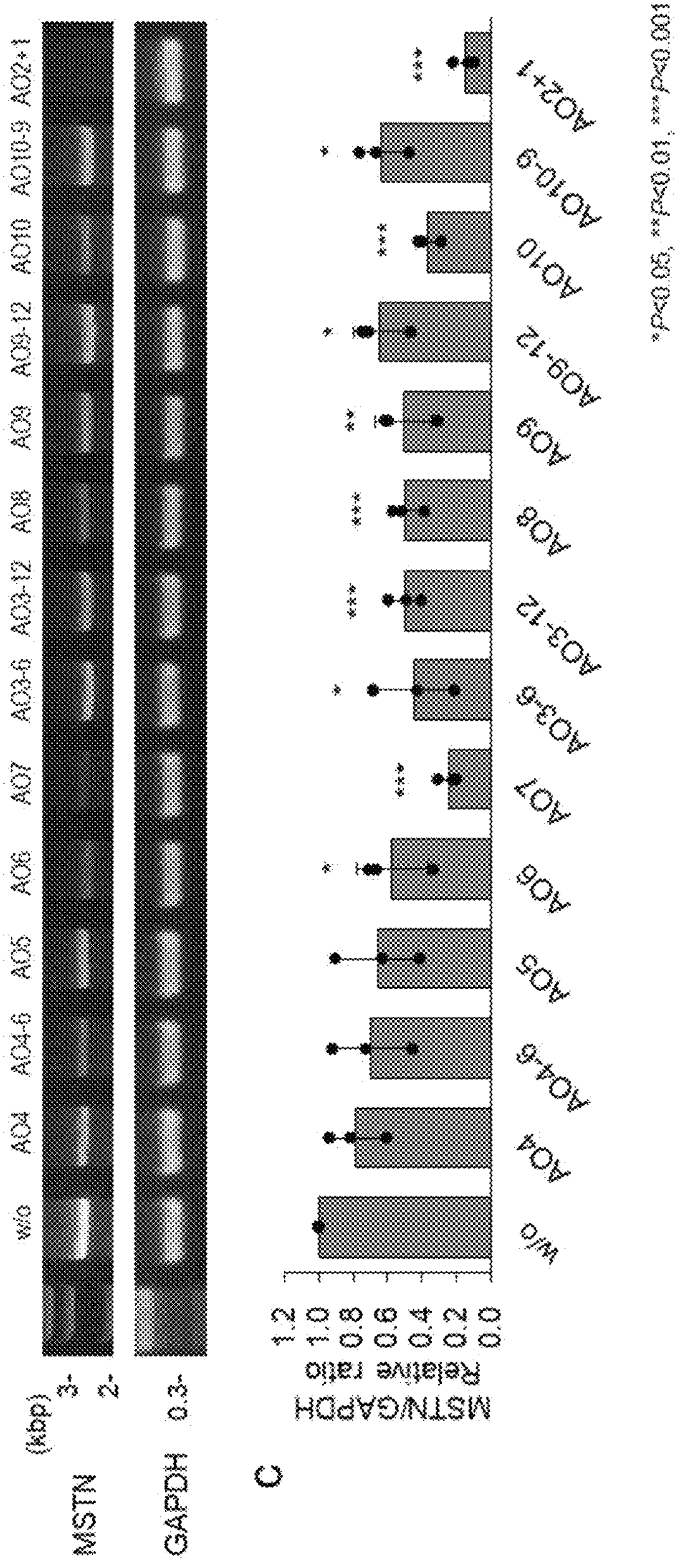

FIG. 4 Comparison of Efficacies between AO2+1 and AOs Designed in Other Regions Each AO was introduced into human rhabdomyosarcoma cells, and the resultant MSTN mRNA was analyzed by RT-PCR. The results are shown.

a) Complementary sequences to AOs in exon 1 are shown. AOs are indicated by brackets below the respective complementary sequences. The numerical figures over the nucleotide sequences (SEQ ID NO:1) indicate the nucleotide numbers with the 5' end nucleotide of exon 1 of MSTN being taken as 1.

b) Results of RT-PCR on MSTN mRNA and GAPDH mRNA of human rhabdomyosarcoma cells are shown. “w/o” means without AO treatment.

c) Relative values are shown with the ratio of MSTN/GAPDH without AO treatment being taken as 1. *P<0.05, P<0.01, *P<0.001.

FIG. 5 a) Validation of Efficacy of AO2+1 in Human Myoblasts. AO2+1 was introduced into human myoblasts and the resultant MSTN mRNA was analyzed by RT-PCR. The results are shown.

b) Results of RT-PCR on MSTN mRNA and GAPDH mRNA of human myoblasts are shown. Relative values are shown with the ratio of MSTN/GAPDH treated with 0 nM AO being taken as 1. P<0.01, *P<0.001.

FIG. 6 a) Validation of Effect of AO2+1 on GDF11 Expression. AO2+1 was introduced into human rhabdomyosarcoma cells, and the resultant MSTN mRNA and GDF11 mRNA were analyzed by RT-PCR. The results are shown.

b) Results of RT-PCR on MSTN mRNA, GDF11 mRNA and GAPDH mRNA of human rhabdomyosarcoma cells are shown. Relative values are shown with the ratio of MSTN/GAPDH and that of GDF11/GAPDH without AO treatment (w/o) being each taken as 1. ***P<0.001.

Figure 7:
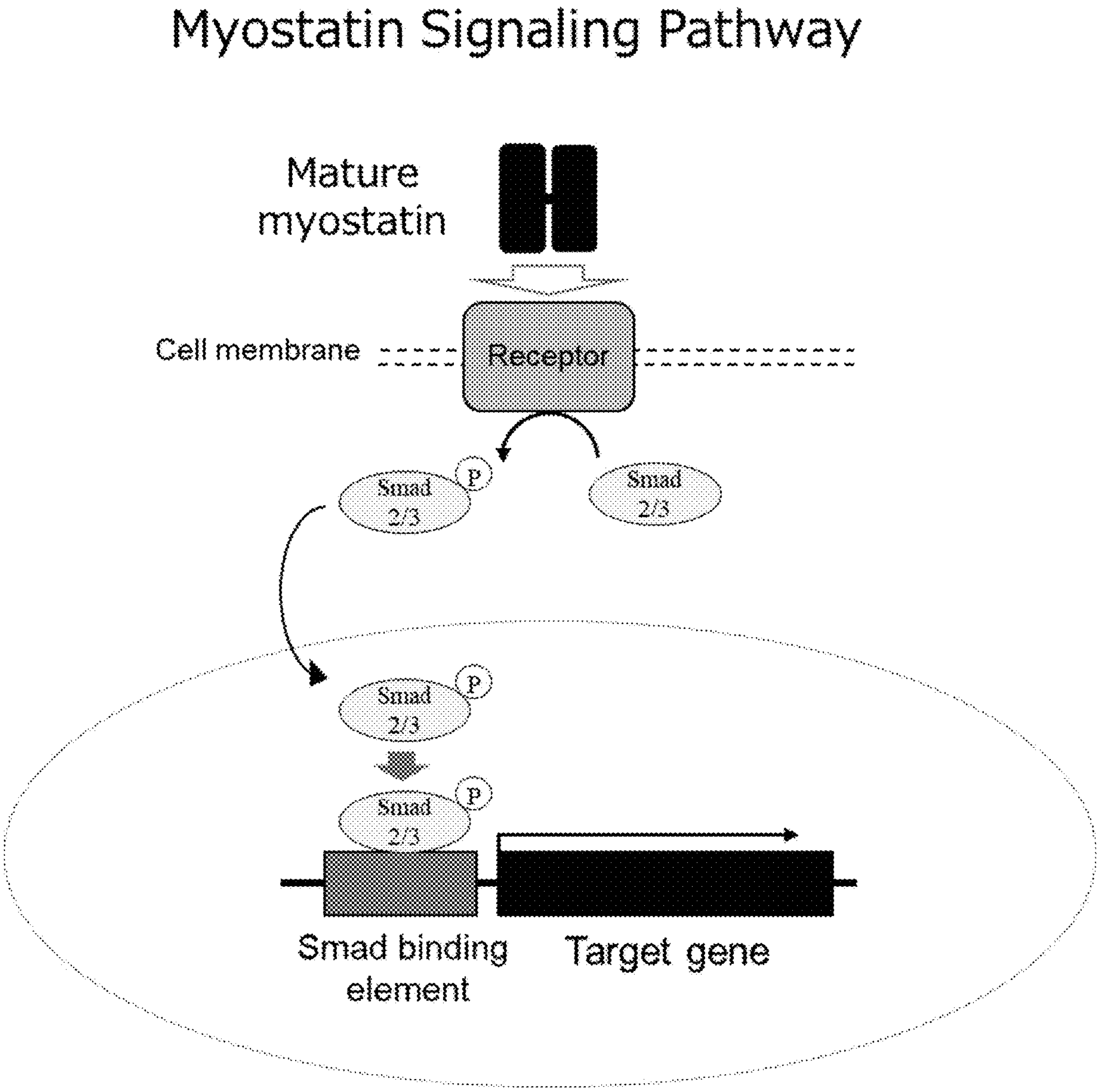

FIG. 7 Myostatin Signaling.

Myostatin activates downstream signal transduction upon binding to its receptor on cell surfaces. When mature myostatin binds to its receptor, Smad2/3 is phosphorylated and the phosphorylated Smad2/3 transits into the nucleus. The phosphorylated Smad2/3 binds to an Smad binding element present in the promoter of a target gene, whereby expression of the target gene is induced.

Figure 8:
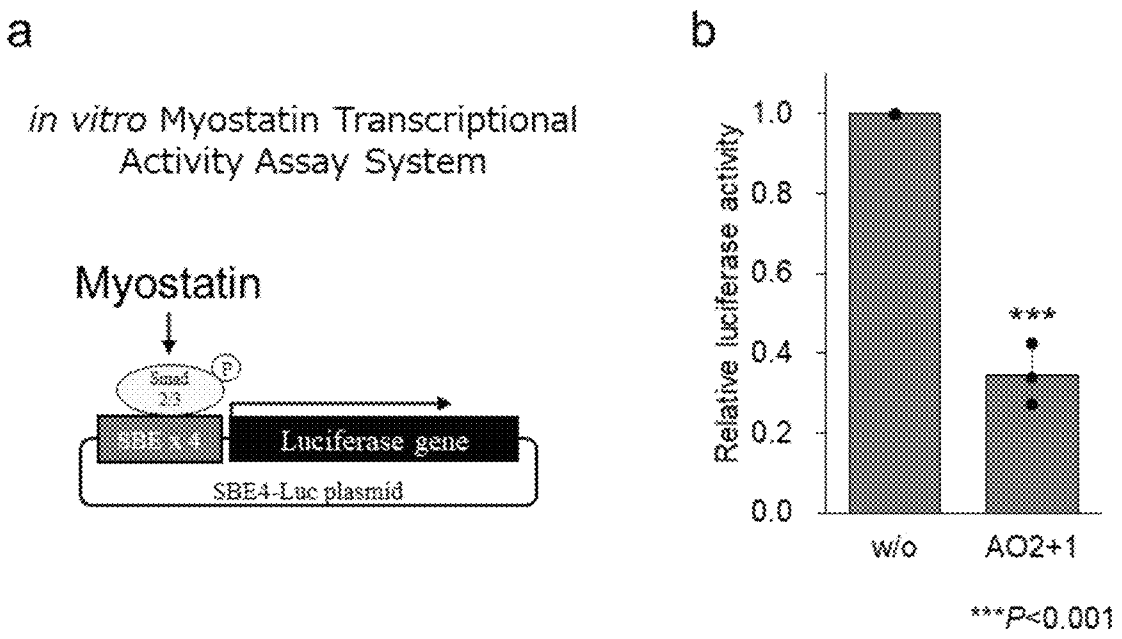

FIG. 8 Decrease in Myostatin Signaling by AO2+1

Results of validation of myostatin signaling in human rhabdomyosarcoma cells processed by AO treatment are shown.

In FIG. 8, a) provides a schematic diagram showing the effect of treatment with AO2+1 on a measuring system for in vitro myostatin transcriptional activity. Myostatin signaling was evaluated in terms of the activity of luciferase whose expression is induced upon treatment with AO2+1 or without AO treatment.

In FIG. 8, b) shows relative values with the result of no AO treatment (w/o) being taken as 1. ***P<0.001.

Figure 9:
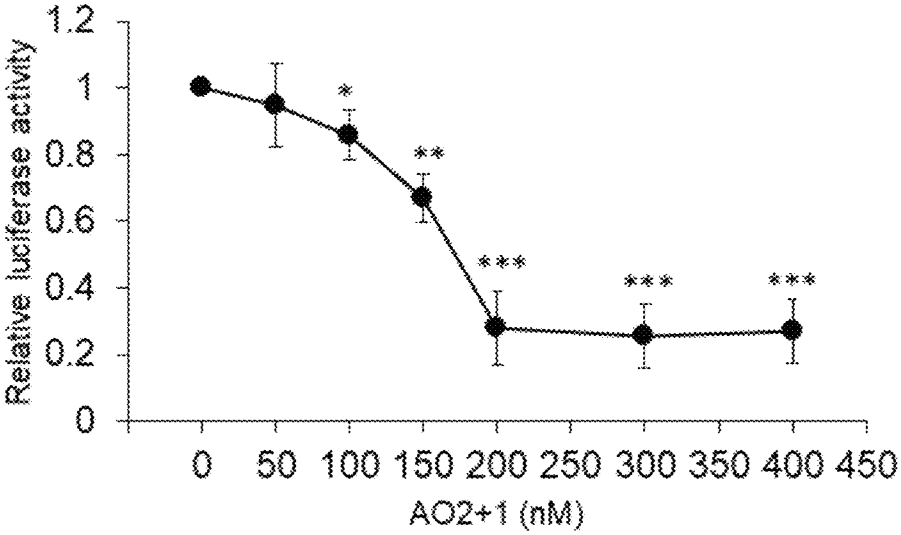

FIG. 9 Decrease in Myostatin Signaling by AO2+1

Results of examination of myostatin signaling in human myoblasts upon AO treatment are shown. Relative values are shown with the result of 0 nM AO treatment being taken as 1. *P<0.05. P<0.01. *P<0.001.

Figure 10:
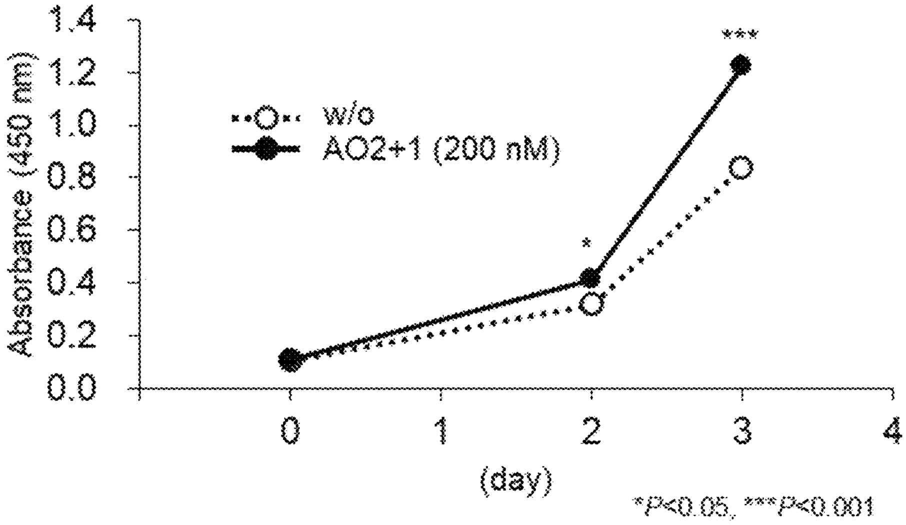

FIG. 10 Promotion of Proliferation of Human Myoblasts by AO2+1

Results of examination of cell proliferation in human myoblasts with or without AO treatment. *P<0.05, ***P<0.001.

FIG. 11 Target Sequence of AO2+1 Preserved across Species.

An alignment of the nucleotide sequences of the amino acid coding region in MSTN exon 1 of human (*Homo sapiens*; SEQ ID NO:30), cattle (*Bos Taurus*; SEQ ID NO:31), pig (*Sus scrofa*; SEQ ID NO:32) and dog (*Canis Lupus familiaris*; SEQ ID NO:33) is shown (5' untranslated region is not included). The target sequence of AO2+1 is shown in boxes (Q).

BEST MODES FOR CARRYING OUT THE INVENTION

Hereinbelow, embodiments of the present invention will be described in detail.

The present invention provides an antisense oligonucleotide of 15-30 bases or a salt or a solvate thereof, wherein the antisense oligonucleotide has a nucleotide sequence complementary to a target site in exon 1 of the myostatin gene and is capable of inhibiting the production of the mRNA of the myostatin gene.

The nucleotide sequence of exon 1 of the human myostatin gene is shown in SEQ ID NO: 1. In the present invention, when the nucleotide sequence of exon 1 of the myostatin gene is the nucleotide sequence as shown in SEQ ID NO: 1, a target site in exon 1 of the myostatin gene may be suitably located within the region of nucleotide Nos. 22-420 of the nucleotide sequence as shown in SEQ ID NO: 1.

Further, in the present invention, the nucleotide sequence of the antisense oligonucleotide may conveniently comprise a sequence consisting of at least 15 consecutive nucleotides in any one of the sequences as shown in SEQ ID NOS: 2-25 (wherein "t" may be "u", and "u" may be "t").

The antisense oligonucleotide may have 18 bases, and the nucleotide sequence of the antisense oligonucleotide may be any one of the sequences as shown in SEQ ID NOS: 2-25 (wherein "t" may be "u", and "u" may be "t").

Nucleotides constituting the antisense oligonucleotide may be either natural DNA, natural RNA, or modified DNA or RNA. Preferably, at least one of the nucleotides is a modified nucleotide.

Examples of modified nucleotides include those in which a sugar is modified [e.g., the hydroxy group at 2'-position of D-ribofuranose is modified as in the case where D-ribofuranose is 2'-O-alkylated or 2'-0,4'-C-alkylenated], those in which a phosphodiester bond is modified (e.g., thioated), those in which a base is modified, combinations of the above-described nucleotides, and so forth. Antisense oligonucleotides in which at least one D-ribofuranose constituting the oligonucleotides is 2'-O-alkylated or 2'-0,4'-C-alkylenated have high RNA binding strength and high resistance to nuclease. Thus, they are expected to produce higher therapeutic effect than natural nucleotides (i.e. oligo DNA or oligo RNA). Further, oligonucleotides in which at least one phosphodiester bond constituting the oligonucleotides is thioated also have high resistance to nuclease and, thus, are expected to produce higher therapeutic effect than natural nucleotides (i.e. oligo DNA or oligo RNA). Oligonucleotides comprising both the modified sugar and the modified phosphate as described above have even higher resistance to nuclease and, thus, are expected to produce even higher therapeutic effect.

With respect to the antisense oligonucleotide, examples of modified sugars include, but are not limited to, D-ribofuranose as 2'-O-alkylated (e.g. 2'-O-methylated, 2'-O-aminoethylated, 2'-O-propylated, 2'-O-allylated, 2'-O-methoxyethylated, 2'-O-butylated, 2'-O-pentylated, or 2'-O-propargylated); D-ribofuranose as 2'-0,4'-C-alkylenated (e.g. 2'-0,4'-C-ethylenated, 2'-0,4'-C-methylenated, 2'-0,4'-C-propylenated, 2'-0,4'-C-tetramethylenated, or 2'-0,4'-C-pentamethylenated); 3'-deoxy-3'-amino-2'-deoxy-D-ribofuranose, 3'-deoxy-3'-amino-2'-deoxy-2'-fluoro-D-ribofuranose, etc.

With respect to the antisense oligonucleotide, examples of the modification of phosphodiester bond include, but are not limited to, phosphorothioate bond, methylphosphonate bond, methylthiophosphonate bond, phosphorodithioate bond and phosphoramidate bond.

With respect to the antisense oligonucleotide, examples of modified bases include, but are not limited to, cytosine as 5-methylated, 5-fluorinated, 5-brominated, 5-iodinated or N4-methylated; thymidine as 5-demethylated (uracil), 5-fluorinated, 5-brominated or 5-iodinated; adenine as N6-methylated or 8-brominated; and guanine as N2-methylated or 8-brominated.

The antisense oligonucleotide of the present invention may be used in the form of a salt. When the antisense oligonucleotide of the present invention is used in a pharmaceutical drug, salts may suitably be pharmaceutically acceptable salts. Examples of such salts include, but are not limited to, alkaline metal salts such as sodium salts, potassium salts or lithium salts; alkaline earth metal salts such as calcium salts or magnesium salts; metal salts such as aluminum salts, iron salts, zinc salts, copper salts, nickel salts or cobalt salts; amine salts including inorganic salts such as ammonium salts and organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts or tris(hydroxymethyl)aminomethane salts; inorganic acid salts including hydrohalogenic acid salts such as hydrofluorides, hydrochlorides, hydrobromides or hydroiodides, as well as nitrates, perchlorates, sulfates or phosphates; organic acid salts including lower alkane sulfonic acid salts such as methanesulfonates, trifluoromethanesulfonates or ethanesulfonates, arylsulfonic acid salts such as benzenesulfonates or p-toluenesulfonates, as well as acetates, malates, fumarates, succinates, citrates, tartrates, oxalates or maleates; and amino acid salts such as glycine salts, lysine salts, arginine salts, ornithine salts, glutamic acid salts or aspartic acid salts. These salts may be prepared by known methods.

The antisense oligonucleotide sometimes occur as a solvate (e.g., hydrate). The antisense oligonucleotide may be such a solvate.

Further, the antisense oligonucleotide may be administered in the form of a prodrug. Examples of such prodrug include, but are not limited to, amides, esters, carbamates, carbonates, ureides and phosphates. These prodrugs may be prepared by known methods.

Methods of synthesizing the antisense oligonucleotide are not particularly limited, and conventional methods may be used. Conventional methods include, but are not limited to, synthesis methods using genetic engineering techniques and chemical synthesis methods. Genetic engineering techniques include, but are not limited to, in vitro transcription synthesis method, method using vectors, and method using PCR cassettes. The vector is not particularly limited. Non-viral vectors such as plasmids, virus vectors, etc. may be used. The chemical synthesis method is not particularly limited. For example, the phosphoramidite method, the H-phosphonate method, or the like may be enumerated. For the chemical synthesis method, a commercially available automated nucleic acid synthesizer, for example, may be used. Generally, amidites are used in the chemical synthesis method. The amidite is not particularly limited. In Examples described later, antisense oligonucleotides were synthesized by the phosphoramidite method using ENA-2CE phosphoramidite and 2'OMe-2-CE phosphoramidite.

As regards phosphoramidite reagents to be used, natural nucleosides and 2'-O-methylnucleosides (i.e., 2'-O-methylguanosine, 2'-O-methyladenosine, 2'-O-methylcytosine and 2'-O-methyluridine) are commercially available. As regards 2'-O-alkylguanosine, -alkyladenosine, -alkylcytosine and -alkyluridine in which the carbon number of the alkyl group is 2-6, the following methods may be employed.

2'-O-aminoethylguanosine, -aminoethyladenosine, -aminoethylcytosine and -aminoethyluridine may be synthesized as previously described (Blommers et al., Biochemistry (1998), 37, 17714-17725).

2'-O-propylguanosine, -propyladenosine, -propylcytosine and -propyluridine may be synthesized as previously described (Lesnik, E. A. et al., Biochemistry (1993), 32, 7832-7838).

For the synthesis of 2'-O-allylguanosine, -allyladenosine, -allylcytosine and -allyluridine, commercially available reagents may be used.

2'-O-methoxyethylguanosine, -methoxyethyladenosine, -methoxyethylcytosine and -methoxyethyluridine may be synthesized as previously described (U.S. Pat. No. 6,261,840 or Martin, P. Helv. Chim. Acta. (1995) 78, 486-504).

2'-O-butylguanosine, -butyladenosine, -butylcytosine and -butyluridine may be synthesized as previously described (Lesnik, E. A. et al., Biochemistry (1993), 32, 7832-7838).

2'-O-pentylguanosine, -pentyladenosine, -pentylcytosine and -pentyluridine may be synthesized as previously described (Lesnik, E. A. et al., Biochemistry (1993), 32, 7832-7838).

For the synthesis of 2'-O-propargylguanosine, -propargyladenosine, -propargylcytosine and -propargyluridine, commercially available reagents may be used.

2'-O,4'-C-methyleneguanosine, 2'-O,4'-C-methyleneadenosine, 5-methylcytosine and 5-methylthymidine may be prepared according to the method described in WO99/14226; and 2'-O,4'-C-alkyleneguanosine, 2'-O,4'-C-alkyleneadenosine, 5-methylcytosine and 5-methylthymidine in which the carbon number of the alkylene group is 2-5 may be prepared according to the method described in WO00/47599.

An antisense oligonucleotide with phophorothioate bonds can be synthesized by coupling phosphoramidite reagents and then reacting sulfur, tetraethylthiuram disulfide (TETD; Applied Biosystems), Beaucage reagent (Glen Research) or a reagent such as xanthan hydride (Tetrahedron Letters, 32, 3005 (1991); J. Am. Chem. Soc. 112, 1253 (1990); PCT/WO98/54198).

As controlled pore glass (CPG) to be used in a DNA synthesizer, 2'-O-methylnucleoside-bound CPG is commercially available. As regards 2'-O,4'-C-methyleneguanosine, 2'-O,4'-C-methyleneadenosine, 5-methylcytosine and 5-methylthymidine, they may be prepared according to the method described in WO99/14226; and as regards 2'-O,4'-C-alkyleneguanosine, 2'-O,4'-C-alkyleneadenosine, 5-methylcytosine and 5-methylthymidine in which the carbon number of the alkylene group is 2-5, they may be prepared according to the method described in WO00/47599. The thus prepared nucleosides may then be bound to CPG as previously described (Oligonucleotide Synthesis, Edited by M. J. Gait, Oxford University Press, 1984). By using the modified CPG (as disclosed in Example 12b of Japanese Unexamined Patent Publication No. Hei7-87982), an oligonucleotide in which a 2-hydroxyethylphosphate group is bound at the 3' end can be synthesized. If 3-amino-Modifier C3 CPG, 3-amino-Modifier C7 CPG or Glyceryl CPG (Glen Research) or 3'-specer C3 SynBase CPG 1000 or 3'-specer C9 SynBase CPG 1000 (Link Technologies) is used, an oligonucleotide in which a hydroxyalkylphosphate group or aminoalkylphosphate group is bound at the 3' end can be synthesized.

The antisense oligonucleotide of the present invention may be used in a pharmaceutical drug. When used in a pharmaceutical drug, the antisense oligonucleotide may be in the form of a pharmaceutically acceptable salt, solvate or prodrug. Therefore, the present invention provides a pharmaceutical drug comprising the above-described antisense oligonucleotide, or a pharmaceutically acceptable salt or solvate thereof. The pharmaceutical drug may be for preventing and/or treating a pathological condition and/or a disease in which myostatin is involved. Examples of the condition and/or disease in which myostatin is involved include, but are not limited to, muscular atrophy (e.g., muscular dystrophy, myopathy, spinal muscular atrophy, sarcopenia and disuse muscle atrophy), as well as conditions and/or diseases in which a therapeutic effect is gained through muscle mass recovery (e.g., cancer cachexia, diabetes, cardiovascular diseases such as cardiac failure or arteriosclerosis, renal diseases such as chronic renal failure, and bone diseases such as inflammatory arthritis). Since myostatin inhibition leads to an increase in skeletal muscle mass, it is believed that myostatin inhibition can be used for treatment of all diseases that present with muscular atrophy regardless of its cause. Increased skeletal muscle mass contributes to increasing the amount of exercise and hence improving metabolism in the whole body. Further, myostatin inhibition can be expected to affect the cardiac muscle to thereby recover its function. In addition, myostatin inhibition is also expected to have the following effects: affecting osteoclasts to thereby inhibit bone resorption; activating the homeostasis capacity of vascular endothelial cells; inducing apoptosis; increasing insulin sensitivity; and so forth.

The antisense oligonucleotide of the present invention or a pharmaceutically acceptable salt, solvate or prodrug thereof (hereinafter, referred to as "active ingredient") may be administered, either alone or together with pharmacologically acceptable carriers, diluents or excipients in appropriate forms of preparations, to mammals (e.g., human, rabbit, dog, cat, rat, mouse, etc.) orally or parenterally. Dose levels may vary depending on the subject to be treated, the target disease, symptoms, administration route, and so on. For example, in the case of use for prevention/treatment of an muscle wasting disease (such as muscular dystrophy), typically about 0.1 to 50 mg/kg body weight, preferably about 0.5 mg/kg body weight, may be administered as a dosage unit in terms of active ingredient at a frequency of about once a week or a month, preferably at a frequency of about once a year, either orally or by intramuscular, subcutaneous or intravenous injection (preferably administered consecutively or on alternate days). In cases of other parenteral administration and oral administration, similar dose levels may be used. If symptoms are very severe, the dosage may be increased accordingly. For other diseases, dose levels may be appropriately increased or decreased with reference to the above-described levels.

Preparations for oral administration include solid or liquid preparations such as tablets (including sugar-coated tablets and film-coated tablets), pills, granules, powders, capsules (including soft capsules), syrups, emulsions and suspensions. These preparations may be prepared according to conventional methods and may contain those carriers, diluents or excipients which are conventionally used in the pharmaceutical formulation procedure. For example, lactose, starch, sucrose, magnesium stearate and the like may be used as carriers or excipients for tablets.

Preparations for parenteral administration include, for example, injections and suppositories. Injections include intravenous injections, subcutaneous injections, intradermal injections, muscle injections, instilment injections, etc. Such injections may be prepared by conventional methods, i.e., by dissolving, suspending or emulsifying the active ingredient in an aseptic, aqueous or oily liquid that is conventionally used in injections. Examples of aqueous liquids for injection include physiological saline and isotonic solutions containing glucose and other auxiliary agents. They may be used in combination with a suitable auxiliary solubilizer such as alcohol (e.g. ethanol), polyalcohol (e.g. propylene glycol, polyethylene glycol), nonionic surfactant [e.g. Polysorbate 80, HCO-50 (polyoxyethylene (50 mol) adduct of hydrogenated castor oil)], etc. Examples of oily liquids for injection include sesame oil and soybean oil. They may be used in combination with an auxiliary solubilizer such as benzyl benzoate, benzyl alcohol, etc. Usually, the prepared injections are filled in appropriate ampoules. Suppositories for administration into the rectum may be prepared by mixing the active ingredient with a conventional suppository base.

It is convenient to formulate the above-described pharmaceutical preparations for oral or parenteral administration into unit dosage forms that would give an appropriate dose of the active ingredient. Examples of such unit dosage forms include tablets, pills, capsules, injections (ampoules), and suppositories. Typically 0.1 to 1000 mg of the active ingredient is preferably contained in each unit dosage form.

The antisense oligonucleotide of the present invention may also be used in food or feed. For example, the antisense oligonucleotide of the present invention may be used as an additive to food or feed, or may be used as a supplement for human or animals. The antisense oligonucleotide of the present invention may be in the form of a salt, a solvate or a prodrug that are acceptable as a food or feed ingredient. Therefore, the present invention provides a food comprising the antisense oligonucleotide or a salt or a solvate thereof that are acceptable as a food ingredient. The present invention also provides a feed comprising the antisense oligonucleotide or a salt or a solvate thereof that are acceptable as a feed ingredient. As one example of the salt, solvate or prodrug that are acceptable as a food or feed ingredient, a pharmaceutically acceptable salt, solvate or prodrug may be given. For details, reference should be had to the foregoing description.

It is possible to promote myocyte proliferation and/or hypertrophy using the antisense oligonucleotide of the present invention. Myocytes are contractile cells that form muscle tissues in human and animals and they include skeletal muscle cell, smooth muscle cell, cardiomyocyte, etc. Myostatin inhibition by the antisense oligonucleotide of the present invention is effective in myoblasts and induces the promotion of myoblast proliferation and differentiation to be capable of eventually causing the proliferation and hypertrophy of myocytes. Myocytes also include precursor cells such as myoblasts. The antisense oligonucleotide of the present invention may be in the form of a salt, a solvate or a prodrug. As one example of salt, solvate or prodrug, a pharmaceutically acceptable salt, solvate or prodrug may be given. For details, reference should be had to the foregoing description. Animals may be those which are expressing myostatin, as exemplified by domestic animals used for work or food, or fishes under culture, specifically by mammals such as cat, dog, sheep, pig or cattle, poultry such as chicken or turkey, and fishes such as salmon, trout, cod fish, tuna or yellowtail. Therefore, the present invention provides an agent for promoting myocyte proliferation and/or hypertrophy, comprising the above-described antisense oligonucleotide or a salt or a solvate thereof. The present invention also provides a method of promoting myocyte proliferation and/or hypertrophy, comprising administering to a subject an effective amount of the antisense oligonucleotide or a salt or a solvate thereof. The subject may be a human or an animal. Animals are as described above. The dosage form, dose level, administration route, administration frequency, etc. of the agent may be determined based on the above-described pharmaceutical drug, and they may be changed appropriately so that the desired effect can be obtained.

Further, the antisense oligonucleotide of the present invention may be used for promoting myogenesis or for inhibiting muscle weakness in human or animals. The antisense oligonucleotide of the present invention may be in the form of a salt, a solvate or a prodrug. As one example of salt, solvate or prodrug, a pharmaceutically acceptable salt, solvate or prodrug may be given. For details, reference should be had to the foregoing description. Animals may be those which are expressing myostatin, as exemplified by domestic animals used for work or food, or fishes under culture, specifically by mammals such as cat, dog, sheep, pig or cattle, poultry such as chicken or turkey, and fishes such as salmon, trout, cod fish, tuna or yellowtail. Therefore, the present invention provides an agent for promoting myogenesis and/or inhibiting muscle weakness, comprising the antisense oligonucleotide or a salt or a solvate thereof. The present invention also provides a method of promoting myogenesis and/or inhibiting muscle weakness, comprising administering to a subject an effective amount of the antisense oligonucleotide or a salt or a solvate thereof. The subject may be a human or an animal. Animals are as described above. The dosage form, dose level, administration route, administration frequency, etc. of the agent may be determined based on the above-described pharmaceutical drug, and they may be changed appropriately so that the desired effect can be obtained.

The food to which the antisense oligonucleotide of the present invention or a salt, a solvate or a prodrug thereof that are acceptable as a food ingredient is added may be any food such as plant-derived foods, animal-derived foods, fungus-derived foods, fresh foods, processed foods, nonessential tasty foods, ingredients to be cooked or seasoned, drinks, health foods, space foods, pet foods, etc.

The following may be added to the food of the present invention: common ingredients such as protein, fat, carbohydrate and sodium; minerals such as potassium, calcium, magnesium and phosphorus; trace elements such as iron, zinc, copper, selenium and chromium; vitamins such as vitamin A, β-carotene, vitamin $B_1$, vitamin $B_2$, vitamin $B_6$, vitamin $B_{12}$, vitamin C, niacin, folic acid, vitamin $D_3$, vitamin E, biotin and pantothenic acid; and other substances such as coenzyme Q10, α-lipoic acid, galacto-oligosaccharide, dietary fiber, excipients (such as water, carboxymethyl cellulose or lactose), sweeteners, flavoring agents (such as malic acid, citric acid or amino acids), and fragrances. When the food of the present invention is provided as a liquid food, water, physiological saline, soup, milk, fruit juice or the like can be used as a liquid in which the food ingredients are dispersed or dissolved. The food of the present invention may be formulated into such forms as powder, granules, tablets or liquid preparations. In order to allow easy intake by patients or elderly persons, the food of the present invention preferably assumes the form of a gel-like product such as jelly.

The feed to which the antisense oligonucleotide of the present invention or a salt, a solvate or a prodrug thereof acceptable as a feed ingredient is added may be any feed such as a single feed (e.g., cereal, vegetable oil meal, rice bran, food manufacturer's by-products (lees), animal feed, etc.) or a mixed feed comprising multiple feed materials and feed additives.

The feed of the present invention may comprise the following additives: antioxidants (such as ethoxyquin, dibutylhydroxytoluene, butylhydroxyanisole, etc.), mold inhibitors (such as propionic acid, calcium propionate, sodium propionate, etc.), thickeners (such as sodium alginate, sodium caseinate, sodium carboxymethylcellulose, propylene glycol, sodium polyacrylate, etc.), emulsifiers (such as glycerin fatty acid ester, sucrose fatty acid ester, sorbitan fatty acid ester, polyoxyethylene sorbitan fatty acid ester, polyoxyethylene glycerin fatty acid ester, etc.), adjusters (such as formic acid), amino acids and the like (such as aminoacetic acid, DL-alanine, L-arginine, L-lysine hydrochloride, L-carnitine, guanidinoacetic acid, sodium L-glutamate, taurine, 2-deamino-2-hydroxymethionine, DL-tryptophan, L-tryptophan, L-threonine, L-valine, DL-methionine, L-lysine sulphate, etc.), vitamins (such as L-ascorbic acid, calcium L-ascorbate, sodium L-ascorbate, sodium-calcium-L-ascorbic acid-2-phosphate ester, magnesium L-ascorbic acid-2-phosphate ester, acetomenaphthone, inositol, dibenzoylthiamine hydrochloride, ergocalciferol, choline chloride, thiamine hydrochloride, pyridoxine hydrochloride, β-carotene, cholecalciferol, DL-α-tocopherol acetate, cyanocobalamin, thiamine mononitrate, nicotinic acid, nicotinamide, p-aminobenzoic acid, calcium D-pantothenate, calcium DL-pantothenate, d-biotin, vitamin A powder, vitamin A oil, vitamin D powder, vitamin D3 oil, vitamin E powder, 25-hydroxycholecalciferol, menadione dimethylpyrimidinol bisulfite, menadione sodium bisulfite, folic acid, riboflavin, riboflavin butyrate ester, etc.), minerals (such as potassium chloride, ferric citrate, calcium gluconate, iron and sodium succinate citrate, magnesium oxide, aluminum hydroxide, zinc carbonate, cobalt carbonate, sodium bicarbonate, magnesium carbonate, manganese carbonate, zinc 2-deamino-2-hydroxymethionine, ferrous DL-threonate, calcium lactate, ferrous fumarate, zinc peptide, iron peptide, copper peptide, manganese peptide, potassium iodide, potassium iodate, calcium iodate, zinc sulfate (dry), zinc sulfate (crystal), zinc methionine sulfate, sodium sulfate (dry), magnesium sulfate (dry), magnesium sulfate (crystal), cobalt sulfate (dry), cobalt sulfate (crystal), ferrous sulfate (dry), copper sulfate (dry), copper sulfate (crystal), manganese sulfate, dipotassium hydrogen phosphate (dry), disodium hydrogen phosphate (dry), potassium dihydrogen phosphate (dry), sodium dihydrogen phosphate (dry), sodium dihydrogen phosphate (crystal), etc.), pigments, synthetic antimicrobials, antibiotics, odorizers, flavoring agents, enzymes, probiotics, organic acids, and so forth.

Intake of the food or feed of the present invention may be performed in such an amount, frequency and a period of intake that the desired effect (e.g., promotion of myogenesis) can be confirmed.

The antisense oligonucleotide of the present invention is capable of inhibiting the production of the mRNA of the myostatin gene. Therefore, the present invention provides an agent for inhibiting the production of the mRNA of the myostatin gene, comprising the antisense oligonucleotide of the present invention. The agent of the present invention may be used as a pharmaceutical drug for human or animals; as an additive to food or feed or a supplement; as a growth promoting agent for animals; or as a reagent for experiments. The antisense oligonucleotide of the present invention may be in the form of a salt, a solvate or a prodrug. As one example of salt, solvate or prodrug, a pharmaceutically acceptable salt, solvate or prodrug may be given. For details, reference should be had to the foregoing description.

The antisense oligonucleotide of the present invention is capable of inhibiting the function of myostatin. Therefore, the present invention provides an inhibitor of the function of myostatin, comprising the antisense oligonucleotide of the present invention. The inhibitor of the function of myostatin of the present invention may be used as a pharmaceutical drug for human or animals; as an additive to food or feed or a supplement; as a growth promoting agent for animals; or as a reagent for experiments. The antisense oligonucleotide of the present invention may be in the form of a salt, a solvate or a prodrug. As one example of salt, solvate or prodrug, a pharmaceutically acceptable salt, solvate or prodrug may be given. For details, reference should be had to the foregoing description.

When the antisense oligonucleotide of the present invention is used as a reagent for experiments, the expression of myostatin can be inhibited by treating myostatin-expressing cells, tissues or organs with the antisense oligonucleotide of the present invention or a salt or a solvate thereof. The antisense oligonucleotide of the present invention or a salt or a solvate thereof may be used in an amount effective for inhibiting the expression of myostatin. The myostatin-expressing cells may be exemplified by myocytes, myosarcoma cells, and cancer cells of digestive organs, lung, esophagus, etc. In addition to naturally occurring cells, myostatin gene-transfected recombinant cells may also be employed. The myostatin-expressing tissues and organs may be exemplified by skeletal muscles, cardiac muscles, blood vessels, kidney, digestive organs, uterus, liver, spleen, lung, etc. The expression of myostatin may be examined by, for example, analyzing the myostatin mRNA in samples by RT-PCR, or by detecting the myostatin protein in samples by Western blotting or by mass spectrometry.

EXAMPLES

Hereinbelow, the present invention will be described in detail with reference to the following Examples. However, the present invention is not limited to these Examples.

[Examples 1-24] Synthesis of Antisense Oligonucleotides (AOs)

The antisense oligonucleotides (AOs) as shown in Table 1 were synthesized. The locations of AO sequences complementary to MSTN pre-mRNA are shown in FIGS. 1 to 4. Modified nucleic acid ENA® (2-O,4-C-Ethylene-bridged Nucleic Acids) was introduced into C (cytosine) and T (thymine) in AO sequences to provide improved affinity and stability.

Synthesis of CaCuggaCCaGCaaCaau (MSTN_Ex1_AO1: SEQ ID NO:2) (Example 1)

Synthesis was performed with an automated nucleic acid synthesizer (DNA/RNA synthesizer model NTS H-6: Nihon Techno Service Co., Ltd.) at 1 mol scale. Concentrations of solvents, reagents and phosphoramidites in each synthesis cycle were the same as those concentrations used in natural oligonucleotide synthesis. Reagents and 2'-O-methylnucleoside phosphoramidites (for adenosine: Product No. 10-3100-10; for guanosine: Product No. 10-3121-10) were available from Glen Research. Solvents used were products from Wako Pure Chemical Industries. Non-natural phosphoramidites used were the following compounds disclosed in Japanese Unexamined Patent Publication No. 2000-297097 at Example 22 (5'-O-dimethoxytrityl-2'-0,4'-C-ethylene-4-N-benzoyl-5-methylcytidine-3'-O-(2-cyanoethyl N,N-diisopropyl)phosphoramidite) and Example 9 (5'-O-dimethoxytrityl-2'-0,4'-C-ethylene-5-methyluridine-3'-O-(2-cyanoethyl N,N-diisopropyl)phosphoramidite). As a solid carrier, universal controlled pore glass (CPG) (Product No. 25-5040; Glen Research) was used. Thus, the titled compound was synthesized. It should be noted here that 15 minutes was set as the time required for condensation of amidites.

Protected oligonucleotide analogs with the sequence of interest were thermally treated with thick aqueous ammonia (55° C., 8 hrs) to thereby cut out oligomers from the support and, at the same time, remove the protective group cyanoethyl on phosphorus atoms and the protective group on nucleobases. The resultant ammonia solution was transferred into Glen-Pak DNA Purification Cartridge (Product No. 60-5100; Glen Research), in which DMT groups were removed according to the protocol recommended by Glen Research. The recovered solution was evaporated under reduced pressure; the residue was purified by reversed phase HPLC [(LC-2a from Shimadzu Corporation; column (Triart C18 from YMC (10×150 mm)); Solution A: 0.1M triethylamine acetate aqueous solution (TEAA), pH 7.0; Solution B: acetonitrile, B %: from 10% to 25% (30 min, linear gradient); 50° C.; 4.7 mL/min; 280 nm]. After distilling off the solvent, the residue was dissolved in 10 mM NaOH solution, and pure water substitution was performed by ultrafiltration using a Microsep centrifugal filtration device (Product No. MCP003C; Nippon Pall). After lyophilization, a compound of interest was obtained.

Synthesis of augCaTTaCaCagCCCCu (MSTN_Ex1_AO2: SEQ ID NO:3) (Example 2)

The compound of Example 2 with the sequence of interest was synthesized in the same manner as described for the compound of Example 1.

The subject compound was identified by negative-ion MALDI-TOFMS (theoretical: 6395.311, found: 6392.585).

The nucleotide sequence of the subject compound is a sequence complementary to nucleotide Nos. 240-257 of *Homo sapiens* myostatin (MSTN), RefSeqGene (LRG 200) on chromosome 2 (Gene Bank accession No. NG_009800.1).

Synthesis of gauuuaguguuuuguCuC (MSTN_Ex1_AO3: SEQ ID NO:4) (Example 3)

The compound of Example 3 with the sequence of interest was synthesized in the same manner as described for the compound of Example 1.

The subject compound was identified by negative-ion MALDI-TOFMS (theoretical: 6226.921, found: 6220.691).

The nucleotide sequence of the subject compound is a sequence complementary to nucleotide Nos.265-282 of *Homo sapiens* myostatin (MSTN), RefSeqGene (LRG 200) on chromosome 2 (Gene Bank accession No. NG_009800.1).

Synthesis of aagTaCaTgCaTTaCaCa (MSTN_Ex1_AO2-6: SEQ ID NO:5) (Example 4)

The compound of Example 4 with the sequence of interest was synthesized in the same manner as described for the compound of Example 1.

The subject compound was identified by negative-ion MALDI-TOFMS (theoretical: 6441.351, found: 6435.8281).

The nucleotide sequence of the subject compound is a sequence complementary to nucleotide Nos. 246-263 of *Homo sapiens* myostatin (MSTN), RefSeqGene (LRG 200) on chromosome 2 (Gene Bank accession No. NG_009800.1).

Synthesis of TaCaTgCaTTaCaCagCC (MSTN_Ex1_AO2-3: SEQ ID NO:6) (Example 5)

The compound of Example 5 with the sequence of interest was synthesized in the same manner as described for the compound of Example 1.

The subject compound was identified by negative-ion MALDI-TOFMS (theoretical: 6445.375, found: 6439.7319).

The nucleotide sequence of the subject compound is a sequence complementary to nucleotide Nos. 243-260 of *Homo sapiens* myostatin (MSTN), RefSeqGene (LRG 200) on chromosome 2 (Gene Bank accession No. NG_009800.1).

Synthesis of CaTTaCaCagCCCCTCTT (MSTN_Ex1_AO2+3: SEQ ID NO:7) (Example 6)

The compound of Example 6 with the sequence of interest was synthesized in the same manner as described for the compound of Example 1.

The subject compound was identified by negative-ion MALDI-TOFMS (theoretical: 6436.396, found: 6430.9077).

The nucleotide sequence of the subject compound is a sequence complementary to nucleotide Nos. 237-254 of *Homo sapiens* myostatin (MSTN), RefSeqGene (LRG 200) on chromosome 2 (Gene Bank accession No. NG_009800.1).

Synthesis of TaCaCagCCCCTCTTTTT (MSTN_Ex1_AO2+6: SEQ ID NO:8) (Example 7)

The compound of Example 7 with the sequence of interest was synthesized in the same manner as described for the compound of Example 1.

The subject compound was identified by negative-ion MALDI-TOFMS (theoretical: 6440.376, found: 6435.562).

The nucleotide sequence of the subject compound is a sequence complementary to nucleotide Nos. 234-251 of *Homo sapiens* myostatin (MSTN), RefSeqGene (LRG 200) on chromosome 2 (Gene Bank accession No. NG_009800.1).

Synthesis of aCagCCCCTCTTTTTCCa (MSTN_Ex1_AO2+9: SEQ ID NO:9) (Example 8)

The compound of Example 8 with the sequence of interest was synthesized in the same manner as described for the compound of Example 1.

The subject compound was identified by negative-ion MALDI-TOFMS (theoretical: 6439.392, found: 6434.6094).

The nucleotide sequence of the subject compound is a sequence complementary to nucleotide Nos. 231-248 of *Homo sapiens* myostatin (MSTN), RefSeqGene (LRG 200) on chromosome 2 (Gene Bank accession No. NG_009800.1).

Synthesis of TgCaTTaCaCagCCCCTC (MSTN_Ex1_AO2+1: SEQ ID NO:10) (Example 9)

The compound of Example 9 with the sequence of interest was synthesized in the same manner as described for the compound of Example 1.

The subject compound was identified by negative-ion MALDI-TOFMS (theoretical: 6449.399, found: 6443.8228).

The nucleotide sequence of the subject compound is a sequence complementary to nucleotide Nos. 239-256 of *Homo sapiens* myostatin (MSTN), RefSeqGene (LRG 200) on chromosome 2 (Gene Bank accession No. NG_009800.1).

Synthesis of gCaTTaCaCagCCCCTCT (MSTN_Ex1_AO2+2: SEQ ID NO:11) (Example 10)

The compound of Example 10 with the sequence of interest was synthesized in the same manner as described for the compound of Example 1.

The subject compound was identified by negative-ion MALDI-TOFMS (theoretical: 6449.399, found: 6443.707).

The nucleotide sequence of the subject compound is a sequence complementary to nucleotide Nos. 238-255 of *Homo sapiens* myostatin (MSTN), RefSeqGene (LRG 200) on chromosome 2 (Gene Bank accession No. NG_009800.1).

Synthesis of aTTaCaCagCCCCTCTTT (MSTN_Ex1_AO2+4: SEQ ID NO: 12) (Example 11)

The compound of Example 11 with the sequence of interest was synthesized in the same manner as described for the compound of Example 1.

The subject compound was identified by negative-ion MALDI-TOFMS (theoretical: 6437.38, found: 6431.9209).

The nucleotide sequence of the subject compound is a sequence complementary to nucleotide Nos. 236-253 of *Homo sapiens* myostatin (MSTN), RefSeqGene (LRG 200) on chromosome 2 (Gene Bank accession No. NG_009800.1).

Synthesis of TTaCaCagCCCCTCTTTT (MSTN_Ex1_AO2+5: SEQ ID NO: 13) (Example 12)

The compound of Example 12 with the sequence of interest was synthesized in the same manner as described for the compound of Example 1.

The subject compound was identified by negative-ion MALDI-TOFMS (theoretical: 6440.376, found: 6434.8232).

The nucleotide sequence of the subject compound is a sequence complementary to nucleotide Nos. 235-252 of *Homo sapiens* myostatin (MSTN), RefSeqGene (LRG 200) on chromosome 2 (Gene Bank accession No. NG_009800.1).

Synthesis of TgTaCagTCTgagagaCa (MSTN_Ex1_AO4: SEQ ID NO:14) (Example 13)

The compound of Example 13 with the sequence of interest was synthesized in the same manner as described for the compound of Example 1.

The subject compound was identified by negative-ion MALDI-TOFMS (theoretical: 6487.336, found: 6481.8237).

The nucleotide sequence of the subject compound is a sequence complementary to nucleotide Nos. 22-39 of *Homo sapiens* myostatin (MSTN), RefSeqGene (LRG_200) on chromosome 2 (Gene Bank accession No. NG_009800.1).

Synthesis of aaTgCaTgTaCagTCTga (MSTN_Ex1_AO4-6: SEQ ID NO:15) (Example 14)

The compound of Example 14 with the sequence of interest was synthesized in the same manner as described for the compound of Example 1.

The subject compound was identified by negative-ion MALDI-TOFMS (theoretical: 6474.333, found: 6468.584).

The nucleotide sequence of the subject compound is a sequence complementary to nucleotide Nos. 28-45 of *Homo sapiens* myostatin (MSTN), RefSeqGene (LRG_200) on chromosome 2 (Gene Bank accession No. NG_009800.1).

Synthesis of TTgCTTTTgagTaaTgCC (MSTN_Ex1_AO5; SEQ ID NO:16) (Example 15)

The compound of Example 15 with the sequence of interest was synthesized in the same manner as described for the compound of Example 1.

The subject compound was identified by negative-ion MALDI-TOFMS (theoretical: 6483.321, found: 6477.7007).

The nucleotide sequence of the subject compound is a sequence complementary to nucleotide Nos. 58-75 of *Homo sapiens* myostatin (MSTN), RefSeqGene (LRG_200) on chromosome 2 (Gene Bank accession No. NG_009800.1).

Synthesis of aaTCaaTaTaaTCTTTTT (MSTN_Ex1_AO6: SEQ ID NO:17) (Example 16)

The compound of Example 16 with the sequence of interest was synthesized in the same manner as described for the compound of Example 1.

The subject compound was identified by negative-ion MALDI-TOFMS (theoretical: 6420.309, found: 6414.5815).

The nucleotide sequence of the subject compound is a sequence complementary to nucleotide Nos. 108-125 of *Homo sapiens* myostatin (MSTN), RefSeqGene (LRG 200) on chromosome 2 (Gene Bank accession No. NG_009800.1).

Synthesis of TTgCTCaCTgTTCTCaTT (MSTN_Ex1_AO7: SEQ ID NO:18) (Example 17)

The compound of Example 17 with the sequence of interest was synthesized in the same manner as described for the compound of Example 1.

The subject compound was identified by negative-ion MALDI-TOFMS (theoretical: 6458.343, found: 6452.9326).

The nucleotide sequence of the subject compound is a sequence complementary to nucleotide Nos. 203-220 of *Homo sapiens* myostatin (MSTN), RefSeqGene (LRG 200) on chromosome 2 (Gene Bank accession No. NG_009800.1).

Synthesis of CTTgaagaTTTagTgTTT (MSTN_Ex1_AO3-6: SEQ ID NO:19) (Example 18)

The compound of Example 18 with the sequence of interest was synthesized in the same manner as described for the compound of Example 1.

The subject compound was identified by negative-ion MALDI-TOFMS (theoretical: 6482.293, found: 6476.7026).

The nucleotide sequence of the subject compound is a sequence complementary to nucleotide Nos. 271-288 of *Homo sapiens* myostatin (MSTN), RefSeqGene (LRG 200) on chromosome 2 (Gene Bank accession No. NG_009800.1).

Synthesis of TCTaTTCTTgaagaTTTa (MSTN_Ex1_AO3-12: SEQ ID NO:20) (Example 19)

The compound of Example 19 with the sequence of interest was synthesized in the same manner as described for the compound of Example 1.

The subject compound was identified by negative-ion MALDI-TOFMS (theoretical: 6452.307, found: 6446.8232).

The nucleotide sequence of the subject compound is a sequence complementary to nucleotide Nos. 277-294 of *Homo sapiens* myostatin (MSTN), RefSeqGene (LRG 200) on chromosome 2 (Gene Bank accession No. NG_009800.1).

Synthesis of TaCTgaggaTTTgTaTCT (MSTN_Ex1_AO8: SEQ ID NO:21) (Example 20)

The compound of Example 20 with the sequence of interest was synthesized in the same manner as described for the compound of Example 1.

The subject compound was identified by negative-ion MALDI-TOFMS (theoretical: 6481.309, found: 6475.8228).

The nucleotide sequence of the subject compound is a sequence complementary to nucleotide Nos. 303-320 of *Homo sapiens* myostatin (MSTN), RefSeqGene (LRG 200) on chromosome 2 (Gene Bank accession No. NG_009800.1).

Synthesis of CaTCTTTgCTgaTgTTag (MSTN_Ex1_AO9; SEQ ID NO:22) (Example 21)

The compound of Example 21 with the sequence of interest was synthesized in the same manner as described for the compound of Example 1.

The subject compound was identified by negative-ion MALDI-TOFMS (theoretical: 6483.321, found: 6477.6953).

The nucleotide sequence of the subject compound is a sequence complementary to nucleotide Nos. 342-359 *Homo sapiens* myostatin (MSTN), RefSeqGene (LRG 200) on chromosome 2 (Gene Bank accession No. NG_009800.1).

Synthesis of gTTgTCTTaTaaCaTCTT (MSTN_Ex1_AO9-12: SEQ ID NO:23) (Example 22)

The compound of Example 22 with the sequence of interest was synthesized in the same manner as described for the compound of Example 1.

The subject compound was identified by negative-ion MALDI-TOFMS (theoretical: 6454.319, found: 6448.7021).

The nucleotide sequence of the subject compound is a sequence complementary to nucleotide Nos. 354-371 of *Homo sapiens* myostatin (MSTN), RefSeqGene (LRG 200) on chromosome 2 (Gene Bank accession No. NG_009800.1).

Synthesis of TgaTCaaTCagTTCCCgg (MSTN_Ex1_AO0; SEQ ID NO:24) (Example 23)

The compound of Example 23 with the sequence of interest was synthesized in the same manner as described for the compound of Example 1.

The subject compound was identified by negative-ion MALDI-TOFMS (theoretical: 6478.357, found: 6472.9458).

The nucleotide sequence of the subject compound is a sequence complementary to nucleotide Nos. 394-411 of *Homo sapiens* myostatin (MSTN), RefSeqGene (LRG 200) on chromosome 2 (Gene Bank accession No. NG_009800.1).

Synthesis of aCaTCaTaCTgaTCaaTC (MSTN_Ex1_AO10-9: SEQ ID NO:25) (Example 24)

The compound of Example 24 with the sequence of interest was synthesized in the same manner as described for the compound of Example 1.

The subject compound was identified by negative-ion MALDI-TOFMS (theoretical: 6430.36, found: 6424.8286).

The nucleotide sequence of the subject compound is a sequence complementary to nucleotide Nos. 403-420 of *Homo sapiens* myostatin (MSTN), RefSeqGene (LRG 200) on chromosome 2 (Gene Bank accession No. NG 009800.1).

TABLE 1

Sequences of the AOs synthesized in Examples are shown. Capital letters represent ENA nucleic acid and small letters 2'OMe.

| Example | Designation | Sequence | SEQ ID NO: |
|---|---|---|---|
| 1 | MSTN_Ex1_AO1 | CaCuggaCCaGCaaCaau | 2 |
| 2 | MSTN_Ex1_AO2 | augCaTTaCaCagCCCCu | 3 |
| 3 | MSTN_Ex1_AO3 | gauuuaguguuuuguCuC | 4 |
| 4 | MSTN_Ex1_AO2-6 | aagTaCaTgCaTTaCaCa | 5 |
| 5 | MSTN_Ex1_AO2-3 | TaCaTgCaTTaCaCagCC | 6 |

TABLE 1-continued

Sequences of the AOs synthesized in Examples are shown. Capital letters represent ENA nucleic acid and small letters 2'OMe.

| Example | Designation | Sequence | SEQ ID NO: |
|---|---|---|---|
| 6 | MSTN_Ex1_AO2+3 | CaTTaCaCagCCCCTCTT | 7 |
| 7 | MSTN_Ex1_AO2+6 | TaCaCagCCCCTCTTTTT | 8 |
| 8 | MSTN_Ex1_AO2+9 | aCagCCCCTCTTTTTCCa | 9 |
| 9 | MSTN_Ex1_AO2+1 | TgCaTTaCaCagCCCCTC | 10 |
| 10 | MSTN_Ex1_AO2+2 | gCaTTaCaCagCCCCTCT | 11 |
| 11 | MSTN_Ex1_AO2+4 | aTTaCaCagCCCCTCTTT | 12 |
| 12 | MSTN_Ex1_AO2+5 | TTaCaCagCCCCTCTTTT | 13 |
| 13 | MSTN_Ex1_AO4 | TgTaCagTCTgagagaCa | 14 |
| 14 | MSTN_Ex1_AO4-6 | aaTgCaTgTaCagTCTga | 15 |
| 15 | MSTN_Ex1_AO5 | TTgCTTTTgagTaaTgCC | 16 |
| 16 | MSTN_Ex1_AO6 | aaTCaaTaTaaTCTTTTT | 17 |
| 17 | MSTN_Ex1_AO7 | TTgCTCaCTgTTCTCaTT | 18 |
| 18 | MSTN_Ex1_AO3-6 | CTTgaagaTTTagTgTTT | 19 |
| 19 | MSTN_Ex1_AO3-12 | TCTaTTCTTgaagaTTTa | 20 |
| 20 | MSTN_Ex1_AO8 | TaCTgaggaTTTgTaTCT | 21 |
| 21 | MSTN_Ex1_AO9 | CaTCTTTgCTgaTgTTag | 22 |
| 22 | MSTN_Ex1_AO9-12 | gTTgTCTTaTaaCaTCTT | 23 |
| 23 | MSTN_Ex1_AO10 | TgaTCaaTCagTTCCCgg | 24 |
| 24 | MSTN_Ex1_AO10-9 | aCaTCaTaCTgaTCaaTC | 25 |

Test Example

Experimental Methods

1. Evaluation of MSTN mRNA Level

Changes in the expression of MSTN mRNA caused by AOs were evaluated by RT-PCR using human rhabdomyosarcoma cells (CRL-2061, ATCC) and human myoblasts (Wada et al., Development 2002, 129; 2987-2995).

AO Transfection

1) Two microliters of each AO (adjusted to a concentration of 50 pmol/μl with MilliQ sterile water) was mixed with 100 μl of Opti-MEM medium (31985070, Thermo Fisher Scientific). For control (without AO treatment), 2 μl of MilliQ sterile water was mixed with the medium.
2) In a separate tube, 4 μl of Lipofectamine™ 2000 Transfection Reagent (11668019, Thermo Fisher Scientific) was mixed with 100 μl of Opti-MEM medium (31985070, Thermo Fisher Scientific).
3) Liquid from 1) and liquid from 2) were mixed and left at room temperature for 20 min. 4) Human rhabdomyosarcoma cells cultured in 12-well plates were washed with PBS once. Then, 800 μl of Opti-MEM medium (31985070, Thermo Fisher Scientific) was added to each well.
5) Liquid from 3) was added to the cells of 4) above (final concentration of AO: 100 nM), and the cells were cultured at 37° C. under 5% $CO_2$ for 3 hrs. Then, the medium was changed to RPMI medium (22400-089, Gibco) containing 10% FBS (10270-106, Gibco), and culture was further continued.
6) Culture of human myoblasts was performed in DMEM medium (043-30085, Wako) containing 20% FBS (10270-106, Gibco) and 2% Ultroser G. AO was transfected to give a final concentration of 0, 100, 200 or 400 nM.

Preparation of RNA

1) Cells transfected with each AO were cultured for 24 hrs and washed with PBS once. Then, 300 μl of RNA extraction reagent in High Pure RNA Isolation Kit (#11828665001, Roche Life Science) was added to the cells.
2) After leaving the cells at room temperature for 5 min, the RNA extraction reagent in each well was collected into a tube.
3) RNA was extracted according to the protocol of High Pure RNA Isolation Kit (#11828665001, Roche Life Science). Finally, 50 μl of RNA solution was obtained.

Reverse Transcription Reaction

1) To 500 ng of RNA, Random primers (#48190011, Thermo Fisher Scientific) and dNTPs (Takara) were added. The resultant solution was incubated at 65° C. for 5 min and at 25° C. for 10 min.
2) To the reaction mixture of 1), M-MLV Reverse Transcriptase (#28025013, Thermo Fisher Scientific), RNaseOUT™ Recombinant Ribonuclease Inhibitor (#10777-019, Thermo Fisher Scientific), DTT (attached to MLVRT) and buffer (attached to MLVRT) were added. The resultant reaction mixture was incubated at 37° C. for 55 min and at 70° C. for 10 min to thereby obtain cDNA.

PCR Reaction and Confirmation of Reaction Products

1) To 2 µl of the resultant cDNA, 1 µl of primer MSTN_Ex1_F1 (5'-agattcactggtgtggcaag-3': SEQ ID NO: 26), 1 µl of primer MSTN R2 (5'-tgcatgacatgtctttgtgc-3': SEQ ID NO: 27), 0.1 µl of TaKaRa Ex Taq® DNA polymerase (#RR001A, Takara), 1.6 µl of dNTPs (attached to TaKaRa Ex Taq®), 2 µl of buffer (10×) and 12.3 µl of MilliQ sterile water were added.
2) The resultant mixture was heated at 94° C. for 3 min.
3) A treatment consisting of 94° C. 0.5 min, 60° C. 0.5 min and 72° C. 1.5 min was performed through 30 cycles.
4) Finally, the reaction mixture was heated at 72° C. for 3 min.
5) After addition of Midri Green Direct DNA Stain (NE-MG06, Nippon Genetics) and Loading buffer (Takara), the PCR products were electrophoresed on 2% agarose gel and visualized with a gel photographing device. Further, the PCR products were electrophoresed and quantified with Agilent2100 bioanalyzer electrophoresis system (Agilent Technology).
6) Above operations 1) to 5) were performed on GAPDH using primer GAPDH H_F (5'-cccttcattgacctcaac-3': SEQ ID NO: 28) and primer GAPDH H_R (5'-ttcacacccatgacgaac-3': SEQ ID NO: 29).
7) Above operations 1) to 5) were performed on GDF11 using primer GDF11Ex1F4 (5'-ctgcagcagatcctggacct-3': SEQ ID NO: 34) and GDF11Ex1R4 (5'-catgaacatgtactcgcact-3': SEQ ID NO: 35).
8) PCR products separated by agarose gel electrophoresis were semiquantified with Image J, and relative comparison was performed taking MSTN/GAPDH without AO treatment as 1.

In the same manner, PCR amplified products quantified with Agilent2100 bioanalyzer electrophoresis system were also compared relatively taking MSTN/GAPDH and GDF11/GAPDH without AO treatment as 1.

2. Evaluation of Myostatin Signaling

Myostatin signaling was evaluated by transfecting human rhabdomyosarcoma cells (CRL-2061, ATCC) and human myoblasts (Wada et al., Development 2002, 129; 2987-2995) with a reporter gene (SBE4-Luc plasmid, #16495, Addgene) and measuring the luminescence of luciferase induced for expression.

AO Transfection

1) Two microliters of AO2+1 (adjusted to a concentration of 50 pmol/µl with MilliQ sterile water) was mixed with 100 µl of Opti-MEM medium (31985070, Thermo Fisher Scientific).
2) In a separate tube, 3 g of SBE4-Luc plasmid, 1 g of pSV-β-Galactosidase Control Vector (E108A, Promega), 4 µl of Lipofectamine™ 3000 Transfection Reagent (11668019, Thermo Fisher Scientific) and 8 µl of P3000 reagent (11668019, Thermo Fisher Scientific) were mixed with 100 µl of Opti-MEM medium (31985070, Thermo Fisher Scientific).
3) Liquid from 1) and liquid from 2) were mixed and left at room temperature for 15 min.
4) Human rhabdomyosarcoma cells cultured in 12-well plates were washed with PBS once. Then, 800 µl of Opti-MEM medium (31985070, Thermo Fisher Scientific) was added to each well.
5) Liquid from 3) was added to the cells of 4) above (final concentration of AO: 100 nM), and the cells were cultured at 37° C. under 5% $CO_2$ for 3 hrs. Then, the medium was changed to RPMI medium (22400-089, Gibco) containing 10% FBS (10270-106, Gibco), and culture was further continued.
6) Culture of human myoblasts was performed in DMEM medium (043-30085, Wako) containing 20% FBS (10270-106, Gibco) and 2% Ultroser G. AOs were transfected to give a final concentration of 0, 50, 100, 150, 200, 300 or 400 nM.

Preparation of Cell Extract

1) Cells 24 hrs after transfection were washed with PBS once. Then, 250 µl of the Reporter Lysis Buffer of Luciferase Assay System with Reporter Lysis Buffer (E4030, Promega) was added to each well.
2) Cell homogenate obtained in 1) was centrifuged at 15000 rpm for 10 min at 4° C. to thereby obtain a supernatant.
3) Quantification of the protein in the cell extract was performed with Qubit® Protein Assay Kit (#Q33211, Thermo Fisher Scientific) according to the protocol.

Measurement of Luciferase Activity

1) Cell extract (100 l) and luciferase substrate (Luciferase Assay System with Reporter Lysis Buffer, #E4030, Promega) (100 l) were mixed on 96-well plates.
2) Luciferase luminescence signal was measured with a multi-label plate reader ARVO™X3 (PerkinElmer).

Measurement of β-Galactosidase Activity

1) Cell extract (100 µl) and β-galactosidase substrate (β-Galactosidase Enzyme Assay System with Reporter Lysis Buffer, #E2000, Promega) (100 µl) were mixed on 96-well plates and incubated at 37° C. for 1 hr.
2) After terminating the reaction by adding 100 µl of 1M sodium carbonate to each well, absorbance at 420 nm was measured with a multi-label plate reader ARVO™X3 (PerkinElmer).

Assay for Activity

The value of luciferase activity was divided by the value of β-galactosidase activity for normalization and evaluated in terms of relative values with the result of measurement of the extract from AO non-treated cells being taken as 1.

3. Measurement of Cell Proliferation

Proliferation of human myoblasts (Wada et al. Development 2002, 129; 2987-2995) was evaluated with Cell Counting Kit-8 (347-07621; Dojindo Laboratories).

AO Transfection

1) AO2+1 (adjusted to a concentration of 50 pmol/µl with MilliQ sterile water) (0.4 l) was mixed with 50 µl of Opti-MEM medium (31985070, Thermo Fisher Scientific).
2) In a separate tube, 0.4 µl of Lipofectamine™ 3000 Transfection Reagent (11668019, Thermo Fisher Scientific) was mixed with 50 µl of Opti-MEM medium (31985070, Thermo Fisher Scientific).
3) The AO solution of 1) and the transfection reagent solution of 2) were mixed and left at room temperature for 15 min.
4) Human myoblasts cultured in 96-well plates were washed with PBS once. Then, the mixture of 3) was added to each well (final concentration of AO: 200 nM), and the cells were cultured at 37° C. under 5% $CO_2$ for 3 hrs. Subsequently, the medium was changed to DMEM medium (043-30085; Wako) containing 20% FBS (10270-106, Gibco) and 2% Ultroser G, and culture was further continued.

Measurement of Viable Cells

Ten microliters of Cell Counting Kit-8 (347-07621; Dojindo Laboratories) was added to each well immediately after AO transfection (day 0) or 2 or 3 days thereafter AO transfection. Cells were cultured at 37° C. under 5% $CO_2$ for 1 hr, and then absorbance at 450 nm was determined for evaluating cell counts.

Nucleotide Sequence Comparison by Alignment

Nucleotide sequence alignment was performed on the amino acid coding region of exon 1 of human myostatin (NM_005259.2), cattle myostatin (NC_037329.1), pig myostatin (NC_010457.5) and dog myostatin (NM_001002959.1). For the alignment, multiple sequence alignment program Clustal Omega of EMBL-EBI (https://www.ebi.ac.uk/Tools/msa/clustalo/) was used. Sequences used in the alignment comparison of nucleotide sequences of exon 1 in the human, cattle, pig and dog myostatins are shown in SEQ ID NOS: 30-33.

Experimental Results

Figure 1:
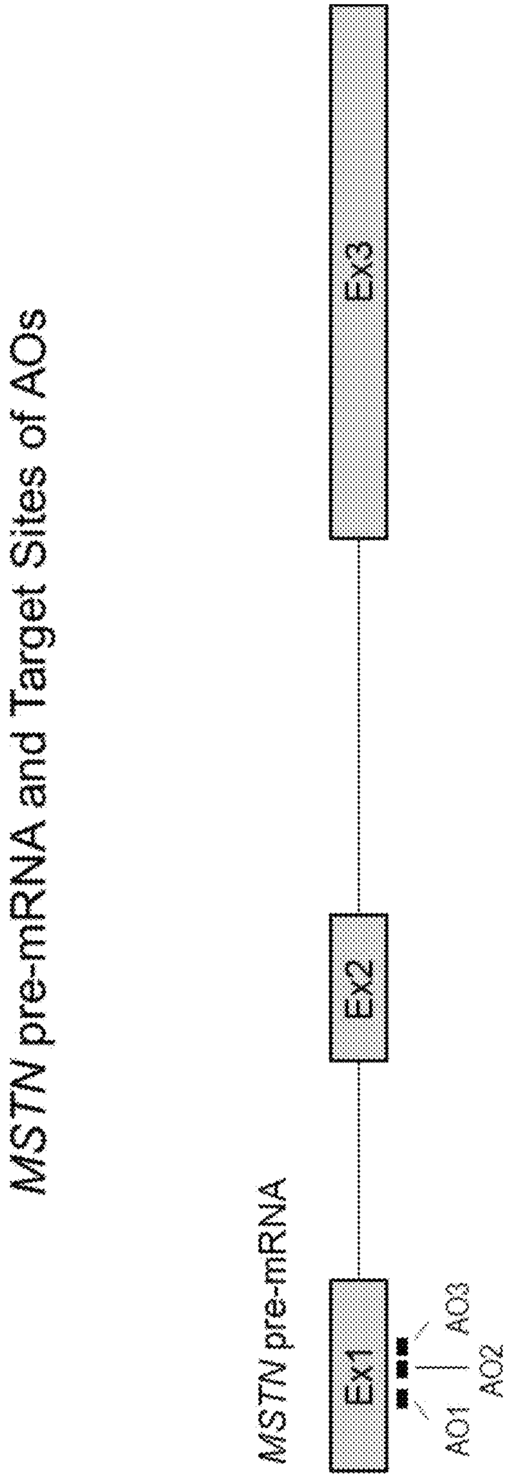
FIG. 1 MSTN pre-mRNA and the Target Sites of AOs

For the purpose of inhibiting the expression of myostatin (MSTN), the present inventors prepared three AOs of 18 bases having a sequence complementary to exon 1 of MSTN pre-mRNA (FIG. 1, FIG. 2*a*). Each AO was designed based on the prediction of binding of a splicing factor in MSTN pre-mRNA. Human rhabdomyosarcoma cells were treated with each AO and the MSTN mRNA level was subsequently examined by RT PCR; at 24 hours after the treatment, the MSTN mRNA level was found to decrease significantly in the AO1 and AO2 treated groups (FIG. 2).

Since AO2 decreased MSTN mRNA by a greater amount than AO1, screening for optimum AO sequences was performed focusing on AO2. First, AOs were prepared in such a way that the sequence of AO2 was shifted by increments of three bases toward the 5' or 3' end and the resultant six AOs targeting nucleotide Nos. 231-263 of MSTN exon 1 (SEQ ID NO: 1) were validated (FIG. 3*a*). As a result of validation on human rhabdomyosarcoma cells, a significant decrease in the MSTN mRNA level was observed 24 hrs after treatment with AO2-6, AO2-3, AO2, AO2+3, AO2+6 and AO2+9 (FIG. 3*b, c*). Among others, AO2+3 was shown to be most effective for decreasing the MSTN mRNA levels. Therefore, the present inventors prepared AOs in such a way that the sequence of AO2+3 was shifted by increments of one base toward the 3' end and the resultant seven AOs targeting nucleotide Nos. 234-257 of MSTN exon 1 (SEQ ID NO: 1) were validated (FIG. 3*a*). As a result of validation on human rhabdomyosarcoma cells, a significant decrease in the MSTN mRNA levels was observed 24 hrs after treatment with AO2, AO2+1, AO2+2, AO2+3, AO2+4, AO2+5 and AO2+6 (FIG. 3*d, e*). As the result of the above-described screening, AO2+1 was obtained as the most effective AO for inhibition of MSTN expression.

Figure 5:
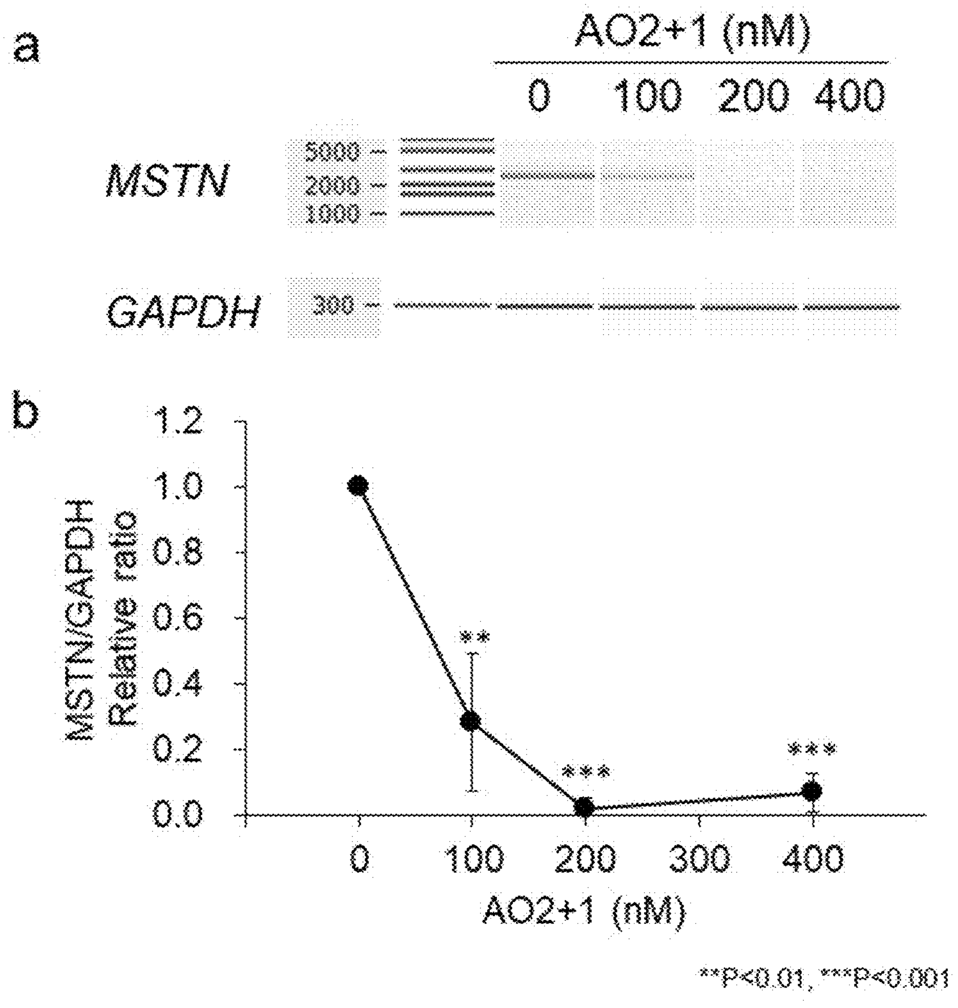
Figure 6:
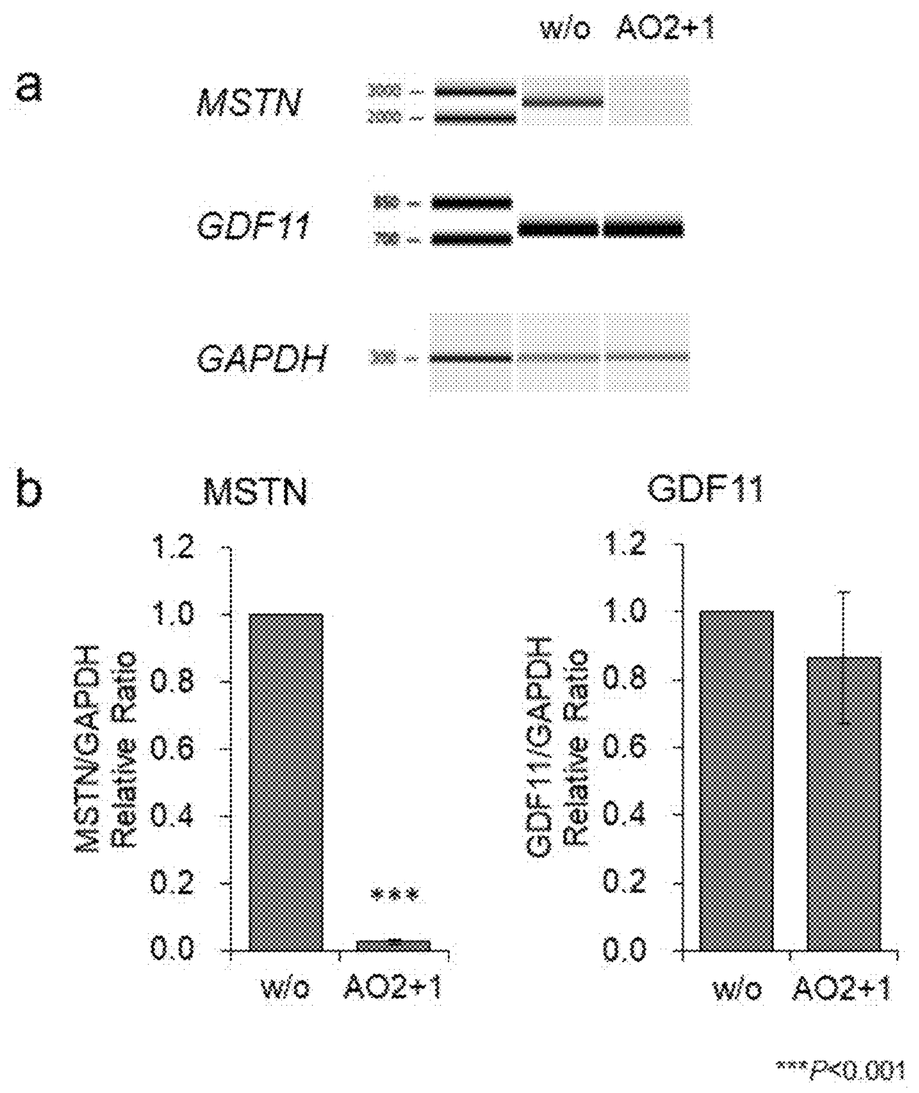

Since it was possible to inhibit MSTN expression by means of AOs targeting exon 1 of MSTN, the present inventors designed AOs in regions other than around AO2+1, and the efficacies of these AOs were compared with the efficacy of AO2+1. Briefly, twelve AOs targeting the range of nucleotide Nos. 22-420 of MSTN exon 1 (SEQ ID NO: 1) were prepared. Human rhabdomyosarcoma cells were treated with each of these AOs and AO2+1 for 24 hrs. As a result, any of the AOs showed a tendency to inhibit the expression of MSTN mRNA (FIG. 4). Among others, AO6, AO7, AO3-6, AO3-12, AO8, AO9, AO9-12, AO10 and AO10-9 significantly decreased MSTN mRNA level. Comparison of MSTN mRNA reduction rates of these AOs revealed that AO2+1 is the most effective. Further, the effect of AO2+1 was also shown on human myoblasts (FIG. 5). On the other hand, AO2+1 did not affect the expression of GDF11 (FIG. 6).

When mature myostatin binds to its receptor on cell surfaces, a transcription factor Smad2/3 is phosphorylated and transits into the nucleus, whereupon the expression of a target gene is induced (FIG. 7). This activation of myostatin signaling was evaluated with an in vitro myostatin transcriptional activity assay system (FIG. 8). This in vitro myostatin transcriptional activity assay system, used a plasmid having a luciferase gene located downstream of an Smad binding promoter. Myostatin signaling was validated by determining the activity of luciferase expressed from this plasmid. As a result of validation of myostatin signaling in human rhabdomyosarcoma cells and human myoblasts, luciferase activity was suppressed by treatment with AO2+1, thus revealing that AO2+1 suppresses myostatin signaling (FIGS. 8 and 9). Further, AO2+1 exhibited a proliferation promotion effect on human myoblasts (FIG. 10).

DISCUSSION

Promoting myogenesis, the inhibition of the function of myostatin has attracted attention as a therapeutic method for muscle wasting diseases. Actually, clinical tests on muscle wasting diseases such as Duchenne muscular dystrophy (DMD) are being carried out using antibodies or peptides that inhibit the function of myostatin. On the other hand, these antibodies or peptides have given rise to the problem of off-target effect (i.e., they may target proteins other than myostatin). For example, mature myostatin which activates myostatin signaling has 90% amino acid identity with mature GDF11 belonging to the same TGF-β family, and therefore, myostatin inhibitory peptides also inhibit GDF11 (Osawa et al., PLoS One, 2015). In contrast, AO2+1 of the present invention does not affect the expression of GDF11 mRNA. Heretofore, AOs that allow the production of out-of-frame mRNA by skipping exon 2 of MSTN pre-mRNA have been developed but clinically useful AOs are yet to be obtained. The AOs of the present invention can inhibit the expression of MSTN mRNA by targeting exon 1 of MSTN mRNA and they differ in terms of action and efficacy from the conventional AOs that allow the production of out-of-frame mRNA. Therefore, the AOs of the present invention are expected to be effective as a therapeutic.

AO2+1 of the present invention is particularly high in efficacy. AO2+1 not only inhibited the expression of MSTN mRNA but also inhibited myostatin signaling and promoted proliferation of myoblasts. There are a number of diseases which are considered to be effectively dealt with by inhibiting myostatin. As a pharmaceutical drug, the AOs of the present invention may be used for preventing and/or treating muscle wasting diseases (e.g., muscular dystrophy, spinal muscular atrophy, sarcopenia, disuse muscle atrophy and the like), cardiovascular diseases (e.g., cardiac failure, arteriosclerosis and the like), renal diseases (e.g., chronic renal failure and the like), bone diseases (e.g., cardiovascular disease is cardiac failure and/or arteriosclerosis and the like), cancer or diabetes. Further, myostatin inhibition leads to an increase in skeletal muscle mass and increases the amount of exercise, thus improving metabolism in the whole body. Further, myostatin inhibition can be expected to affect the cardiac muscle to thereby recover its function thereof. Still further, myostatin inhibition is expected to have the following effects: affecting osteoclasts to thereby inhibit bone resorption; activating the homeostasis capacity of vascular endothelial cells; inducing apoptosis; increasing insulin sensitivity; and so forth.

The target sequence of AO2+1 of the present invention is also conserved in cattle and pig. Therefore, AO2+1 is also applicable to growth promotion of these domestic animals (FIG. 11). Since inhibition of MSTN expression by AO administration to domestic animals is not categorized as the preparation of recombinant organisms, AO2+1 of the present invention is easy to apply. Similarly, AO2+1 is also considered to be effective in dog and, hence, considered to be applicable to muscle weakness in dogs as a companion animal (FIG. 11).

All publications, patents and patent applications cited herein are incorporated herein by reference in their entirety.

INDUSTRIAL APPLICABILITY

The present invention is applicable as a nucleic acid drug that inhibits expression of the mRNA of the myostatin gene.

[SEQUENCE LISTING FREE TEXT]

<SEQ ID NO: 1> shows MSTN exon 1 nucleotide sequence information.

(506 bases in total. Start codon (atg) is shown in a box (□).)

```
agattcactggtgtggcaagttgtctctcagactgtacatgcattaaaattttgcttggc   60
attactcaaaagcaaaagaaaagtaaaaggaagaaacaagaacaagaaaaaagattatat  120
tgattttaaaatcatgcaaaaactgcaactctgtgtttatatttacctgtttatgctgat  180

tgttgctggtccagtggatctaaatgagaacagtgagcaaaaagaaaatgtggaaaaaga  240
ggggctgtgtaatgcatgtacttggagacaaaacactaaatcttcaagaatagaagccat  300
taagatacaaatcctcagtaaacttcgtctggaaacagctcctaacatcagcaaagatgt  360
tataagacaacttttacccaaagctcctccactccgggaactgattgatcagtatgatgt  420
ccagagggatgacagcagcgatggctctttggaagatgacgattatcacgctacaacgga  480
aacaatcattaccatgcctacagagt                                    506
```

<SEQ ID NOS: 2-25> show the nucleotide sequences of the AOs synthesized in Examples. Nucleotides constituting the antisense oligonucleotide may be either natural DNA, natural RNA, chimeric DNA/RNA, or modified DNA, RNA or DNA/RNA. Preferably, at least one of the nucleotides is a modified nucleotide.

<SEQ ID NOS: 26-29> show the nucleotide sequences of the primers used in Test Example.

<SEQ ID NOS: 30-33> show the sequences used in alignment comparison of myostatin exon 1 nucleotide sequences of human, cattle, pig and dog. Alignment comparison was performed using Multiple Sequence Alignment of EMBL-EBI. The amino acid coding region in exon 1 alone was compared. Indicated within parentheses ( ) are designations found in BLAST. The sequence shown in boxes (Q) is the target sequence of AO2+1.

Ex1 (ORF)

> Human (*Homo sapiens*)

(SEQ ID NO: 30)

atgcaaaaactgcaactctgtgtttatatttacctgtttatgctgattgttgctggtccagtggatctaaa tgagaacagtgagcaaaaagaaaatgtggaaaaagaggggctgtgtaataatgcatgtacttggagacaaaaca ctaaatcttcaagaatagaagccattaagatacaaatcctcagtaaacttcgtctggaaacagctcctaac atcagcaaagatgttataagacaacttttacccaaagctcctccactccgggaactgattgatcagtatga tgtccagagggatgacagcagcgatggctctttggaagatgacgattatcacgctacaacggaaacaatca ttaccatgcctacagagt > Cattle (*Bos Taurus*)

(SEQ ID NO: 31)

atgcaaaaactgcaaatctctgtttatatttacctatttatgctgattgttgctggcccagtggatctgaa tgagaacagcgagcaaaaagaaaatgtggaaaaagaggggctgtgtaataatgcatgtttgtggagggaaaaca ctacatcctcaagactagaagccataaaaatccaaatcctcagtaaacttcgcctggaaacagctcctaac atcagcaaagatgctatcagacaacttttgcccaaggctcctccactcctggaactgattgatcagttcga tgtccagagagatgccagcagtgacggctccttggaagacgatgactaccacgccaggacggaaacggtca ttaccatgcccacggagt -continued > Pig (*Sus scrofa*)
atgcaaaaactgcaaatctatgtttatatttacctgtttatgctgattgttgctggtcccgtggatctgaa tgagaacagcgagcaaaaagaaaatgtggaaaaagaggggctgtgtaataatgcatgtatggagacaaaaca ctaaatcttcaagactagaagccataaaaattcaaatcctcagtaaacttcgcctggaaacagctcctaac attagcaaagatgctataagacaacttttgcccaaagctcctccactccgggaactgattgatcagtacga tgtccagagagatgacagcagtgatggctccttggaagatgatgattatcacgctacgacggaaacgatca ttaccatgcctacagagt (SEQ ID NO: 32)

> Dog (*Canis Lupus familiaris*)

(SEQ ID NO: 33)

atgcagagactgcaaatctgtgtttatatttacctgtttgtgctgattgttgctggcccagtcgatctaag tgagaacagtgagcaaaaagaaaatgtggaaaaagaggggctgtgtaataatgcatgtatggagacaaaaca ctaagtcttcaaggatagaagccataaaaattcaaatcctcagcaaacttcgcctggaaacggctcccaac atcagcagagatgctgtcagacaactcttgccgcgggctcctccgctgcgggagctgatcgaccagtacga cgtccagagggatgacagcagcgacggctccctggaggacgacgactaccacgccaccaccgagacggtca ttgccatgcccgccgaga <SEQ ID NOS: 34 and 35> show the nucleotide sequences of primers GDF11Ex1F4 and GDF11Ex1R4.

The invention claimed is:

1. An antisense oligonucleotide or a salt or a solvate thereof, wherein the antisense oligonucleotide has a nucleotide sequence complementary to a target site in exon 1 of the myostatin gene and is capable of inhibiting the production of mRNA of the myostatin gene by inhibiting splicing of the myostatin gene, wherein the antisense oligonucleotide has 18 bases, and wherein the nucleotide sequence of the antisense oligonucleotide is any one of the sequences set forth in SEQ ID NOs: 3, 7, 8, 9, 10, 11, 12, 13, 18 and 24 (wherein "t" may be "u", and "u" may be "t").

2. The antisense oligonucleotide or a salt or a solvate thereof of claim 1, wherein the nucleotide sequence of exon 1 of the myostatin gene is the nucleotide sequence as shown in SEQ ID NO: 1, and the target site in exon 1 of the myostatin gene is located within the region of nucleotide Nos. 22-420 of the nucleotide sequence as shown in SEQ ID NO: 1.

3. The antisense oligonucleotide or a salt or a solvate thereof of claim 1, wherein at least one nucleotide is modified.

4. The antisense oligonucleotide or a salt or a solvate thereof of claim 3, wherein the sugar constituting the modified nucleotide is D-ribofuranose and the hydroxy group at 2'-position of D-ribofuranose is modified.

5. The antisense oligonucleotide or a salt or a solvate thereof of claim 4, wherein D-ribofuranose is 2'-O-alkylated and/or 2'-O,4'-C-alkylenated.

6. A pharmaceutical drug comprising the antisense oligonucleotide of claim 1 or a pharmaceutically acceptable salt or solvate thereof.

7. The pharmaceutical drug of claim 6 for preventing and/or treating a pathological condition and/or a disease in which myostatin is involved.

8. The pharmaceutical drug of claim 7, wherein the condition and/or disease in which myostatin is involved is muscular atrophy.

9. The pharmaceutical drug of claim 8, wherein muscular atrophy is at least one selected from the group consisting of muscular dystrophy, myopathy, spinal muscular atrophy, sarcopenia and disuse muscle atrophy.

10. The pharmaceutical drug of claim 7, wherein the condition and/or disease in which myostatin is involved is a condition and/or a disease in which therapeutic effect is gained through muscle mass recovery.

11. The pharmaceutical drug of claim 10, wherein the condition and/or disease in which therapeutic effect is gained through muscle mass recovery is at least one selected from the group consisting of cancer cachexia, diabetes, cardiovascular diseases, renal diseases and bone diseases.

12. The pharmaceutical drug of claim 11, wherein the cardiovascular disease is cardiac failure and/or arteriosclerosis; the renal disease is chronic renal failure; and the bone disease is inflammatory arthritis.

13. A food comprising the antisense oligonucleotide of claim 1 or a salt or a solvate thereof that are acceptable as a food ingredient.

14. A feed comprising the antisense oligonucleotide of claim 1 or a salt or solvate thereof that are acceptable as a feed ingredient.

15. An agent for promoting myocyte proliferation and/or hypertrophy, comprising the antisense oligonucleotide or a salt or a solvate thereof of claim 1.

16. An agent for increasing muscle mass and/or suppressing muscle weakness, comprising the antisense oligonucleotide or a salt or a solvate thereof of claim 1.

17. An agent for inhibiting the production of the mRNA of the myostatin gene, comprising the antisense oligonucleotide or a salt or a solvate thereof of claim 1.

18. An inhibitor of the function of myostatin, comprising the antisense oligonucleotide or a salt or a solvate thereof of claim 1.

19. A method of preventing and/or treating a disease in which myostatin is involved, comprising administering to a subject an effective amount of the antisense oligonucleotide or a salt or a solvate thereof of claim 1.

20. A method of promoting myocyte proliferation and/or hypertrophy, comprising administering to a subject an effective amount of the antisense oligonucleotide or a salt or a solvate thereof of claim 1.

21. A method of increasing muscle mass and/or suppressing muscle weakness, comprising administering to a subject an effective amount of the antisense oligonucleotide or a salt or a solvate thereof of claim 1.

22. A method of inhibiting the production of the mRNA of the myostatin gene, comprising administering to a subject an effective amount of the antisense oligonucleotide or a salt or a solvate thereof of claim 1.

23. A method of inhibiting the function of myostatin, comprising administering to a subject an effective amount of the antisense oligonucleotide or a salt or a solvate thereof of claim 1.

* * * * *

SEQUENCE LISTING

```
<160> NUMBER OF SEQ ID NOS: 35

<210> SEQ ID NO 1
<211> LENGTH: 506
<212> TYPE: DNA
<213> ORGANISM: Homo sapiens

<400> SEQUENCE: 1

agattcactg gtgtggcaag ttgtctctca gactgtacat gcattaaaat tttgcttggc      60

attactcaaa agcaaaagaa aagtaaaagg aagaaacaag aacaagaaaa aagattatat     120

tgattttaaa atcatgcaaa aactgcaact ctgtgtttat atttacctgt ttatgctgat     180

tgttgctggt ccagtggatc taaatgagaa cagtgagcaa aaagaaaatg tggaaaaaga     240

ggggctgtgt aatgcatgta cttggagaca aaacactaaa tcttcaagaa tagaagccat     300

taagatacaa atcctcagta aacttcgtct ggaaacagct cctaacatca gcaaagatgt     360

tataagacaa cttttaccca aagctcctcc actccgggaa ctgattgatc agtatgatgt     420

ccagagggat gacagcagcg atggctcttt ggaagatgac gattatcacg ctacaacgga     480

aacaatcatt accatgccta cagagt                                          506


<210> SEQ ID NO 2
<211> LENGTH: 18
<212> TYPE: RNA
<213> ORGANISM: Artificial Sequence
<220> FEATURE:
<223> OTHER INFORMATION: Antisense oligonucleotide

<400> SEQUENCE: 2

cacuggacca gcaacaau                                                    18
```

-continued

<210> SEQ ID NO 3
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 3
augcattaca cagccccu 18

<210> SEQ ID NO 4
<211> LENGTH: 18
<212> TYPE: RNA
<213> ORGANISM: Artificial Sequence
<220> FEATURE:
<223> OTHER INFORMATION: Antisense oligonucleotide

<400> SEQUENCE: 4
gauuuagugu uuugucuc 18

<210> SEQ ID NO 5
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 5
aagtacatgc attacaca 18

<210> SEQ ID NO 6
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 6
tacatgcatt acacagcc 18

<210> SEQ ID NO 7
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 7
cattacacag cccctctt 18

<210> SEQ ID NO 8
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 8
tacacagccc ctcttttt 18

<210> SEQ ID NO 9
<211> LENGTH: 18
<212> TYPE: DNA
<213> ORGANISM: Artificial Sequence
<220> FEATURE:
<223> OTHER INFORMATION: Antisense oligonucleotide -continued

<400> SEQUENCE: 9
acagcccctc tttttcca 18

<210> SEQ ID NO 10
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 10
tgcattacac agcccctc 18

<210> SEQ ID NO 11
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 11
gcattacaca gcccctct 18

<210> SEQ ID NO 12
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 12
attacacagc ccctcttt 18

<210> SEQ ID NO 13
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 13
ttacacagcc cctctttt 18

<210> SEQ ID NO 14
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 14
tgtacagtct gagagaca 18

<210> SEQ ID NO 15
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 15
aatgcatgta cagtctga 18

<210> SEQ ID NO 16
<211> LENGTH: 18

-continued

<212> TYPE: DNA
<213> ORGANISM: Artificial Sequence
<220> FEATURE:
<223> OTHER INFORMATION: Antisense oligonucleotide

<400> SEQUENCE: 16
ttgcttttga gtaatgcc 18

<210> SEQ ID NO 17
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 17
aatcaatata atcttttt 18

<210> SEQ ID NO 18
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 18
ttgctcactg ttctcatt 18

<210> SEQ ID NO 19
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 19
cttgaagatt tagtgttt 18

<210> SEQ ID NO 20
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 20
tctattcttg aagattta 18

<210> SEQ ID NO 21
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 21
tactgaggat ttgtatct 18

<210> SEQ ID NO 22
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 22
catctttgct gatgttag 18

<210> SEQ ID NO 23
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 23
gttgtcttat aacatctt 18

<210> SEQ ID NO 24
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 24
tgatcaatca gttcccgg 18

<210> SEQ ID NO 25
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 25
acatcatact gatcaatc 18

<210> SEQ ID NO 26
<211> LENGTH: 40
<212> TYPE: DNA
<213> ORGANISM: Artificial Sequence
<220> FEATURE:
<223> OTHER INFORMATION: Primer

<400> SEQUENCE: 26
agattcactg gtgtggcaag agattcactg gtgtggcaag 40

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tgcatgacat gtctttgtgc 20

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
cccttcattg acctcaac 18

<210> SEQ ID NO 29
<211> LENGTH: 18
<212> TYPE: DNA
<213> ORGANISM: Artificial Sequence -continued
<220> FEATURE:
<223> OTHER INFORMATION: Primer

<400> SEQUENCE: 29
ttcacaccca tgacgaac 18

<210> SEQ ID NO 30
<211> LENGTH: 373
<212> TYPE: DNA
<213> ORGANISM: Homo sapiens

<400> SEQUENCE: 30
atgcaaaaac tgcaactctg tgtttatatt tacctgttta tgctgattgt tgctggtcca 60
gtggatctaa atgagaacag tgagcaaaaa gaaaatgtgg aaaaagaggg gctgtgtaat 120
gcatgtactt ggagacaaaa cactaaatct tcaagaatag aagccattaa gatacaaatc 180
ctcagtaaac ttcgtctgga aacagctcct aacatcagca aagatgttat aagacaactt 240
ttacccaaag ctcctccact ccgggaactg attgatcagt atgatgtcca gagggatgac 300
agcagcgatg gctctttgga agatgacgat tatcacgcta caacggaaac aatcattacc 360
atgcctacag agt 373

<210> SEQ ID NO 31
<211> LENGTH: 373
<212> TYPE: DNA
<213> ORGANISM: Bos taurus

<400> SEQUENCE: 31
atgcaaaaac tgcaaatctc tgtttatatt tacctattta tgctgattgt tgctggccca 60
gtggatctga atgagaacag cgagcagaag gaaaatgtgg aaaaagaggg gctgtgtaat 120
gcatgtttgt ggagggaaaa cactacatcc tcaagactag aagccataaa aatccaaatc 180
ctcagtaaac ttcgcctgga aacagctcct aacatcagca aagatgctat cagacaactt 240
ttgcccaagg ctcctccact cctggaactg attgatcagt tcgatgtcca gagagatgcc 300
agcagtgacg gctccttgga agacgatgac taccacgcca ggacggaaac ggtcattacc 360
atgcccacgg agt 373

<210> SEQ ID NO 32
<211> LENGTH: 373
<212> TYPE: DNA
<213> ORGANISM: Sus scrofa

<400> SEQUENCE: 32
atgcaaaaac tgcaaatcta tgtttatatt tacctgttta tgctgattgt tgctggtccc 60
gtggatctga atgagaacag cgagcaaaag gaaaatgtgg aaaaagaggg gctgtgtaat 120
gcatgtatgt ggagacaaaa cactaaatct tcaagactag aagccataaa aattcaaatc 180
ctcagtaaac ttcgcctgga aacagctcct aacattagca aagatgctat aagacaactt 240
ttgcccaaag ctcctccact ccgggaactg attgatcagt acgatgtcca gagagatgac 300
agcagtgatg gctccttgga agatgatgat tatcacgcta cgacggaaac gatcattacc 360
atgcctacag agt 373

<210> SEQ ID NO 33
<211> LENGTH: 373
<212> TYPE: DNA
<213> ORGANISM: Canis lupus -continued

```
<400> SEQUENCE: 33

atgcagagac tgcaaatctg tgtttatatt tacctgtttg tgctgattgt tgctggccca     60

gtcgatctaa gtgagaacag tgagcaaaaa gaaaatgtgg aaaaggaggg gctgtgtaat    120

gcatgtatgt ggaggcaaaa cactaagtct tcaaggatag aagccataaa aattcaaatc    180

ctcagcaaac ttcgcctgga aacggctccc aacatcagca gagatgctgt cagacaactc    240

ttgccgcggg ctcctccgct gcgggagctg atcgaccagt acgacgtcca gagggatgac    300

agcagcgacg gctccctgga ggacgacgac taccacgcca ccaccgagac ggtcattgcc    360

atgcccgccg aga                                                        373


<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34

ctgcagcaga tcctggacct                                                  20


<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35

catgaacatg tactcgcact                                                  20
```